(12) United States Patent
Grand-Perrett et al.

(10) Patent No.: US 6,673,555 B1
(45) Date of Patent: Jan. 6, 2004

(54) METHODS OF USING SCAP ANTAGONISTS

(75) Inventors: Thierry André Régis Grand-Perrett, Les Ulis (FR); Marc Issandou, Les Ulis (FR)

(73) Assignee: SmithKline Beecham Corporation, Philadelphia, PA (US)

( * ) Notice: Subject to any disclaimer, the term of this patent is extended or adjusted under 35 U.S.C. 154(b) by 20 days.

(21) Appl. No.: 09/615,095

(22) Filed: Jul. 13, 2000

(30) Foreign Application Priority Data

Jul. 17, 1999 (GB) .............................................. 9916757

(51) Int. Cl.$^7$ .......................... G01N 33/53; C12Q 1/60; A61K 38/00; A01N 25/00; C07K 14/00
(52) U.S. Cl. .............................. 435/7.1; 435/11; 514/2; 514/12; 514/824; 514/866; 530/350; 530/359
(58) Field of Search ........................... 435/69.1, 4, 7.1, 435/11; 514/2, 12, 824, 866; 530/350, 359

(56) References Cited

U.S. PATENT DOCUMENTS 6,372,724 B1   4/2002   Pelleg et al.
6,387,913 B1   5/2002   Mustafa

OTHER PUBLICATIONS

Horton et al., "Sterol regulatory element–binding proteins: activators of cholesterol and fatty acid biosynthesis," *Current Opinion in Lipidology* 10:143–150 (1999).
Kovanen et al., "Regulation of the low density lipoprotein (B/E) receptor," *Advances in Vascular Biology* 5:165–185 (1999).
Aguilar–Salinas et al., "Metabolic modes of action of the statins in the hyperlipoproteinemias," *Atherosclerosis* 141:203–207 (1998).
Chan et al., "Jasmine green tea epicatechins are hypolipidemic in hamsters (*Mesocricetus auratus*) fed a high fat diet," *J. Nutr.* 129(6):1094–1101 (Jun. 1999).
Draijer et al., "HOE 402 lowers serum cholesterol levels by reducing VLDL–lipid production, and not by induction of the LDL receptor, and reduces atherosclerosis in wild–type and LDL receptor–deficient mice," *Biochemical Pharmacology* 63:1755–1761 (2002).
Grand–Perret et al., "SCAP ligands are potent new lipid–lowering drugs," *Nature Medicine* 7(12):1332–1338 (Dec. 2001).
Hoffmann et al., "Cholesterol lowering action of HOE 402 in the normolipidemic and hypercholesterolemic Golden Syrian hamster," *Biochimica et Biophysica Acta* 1299:95–102 (1996).
Korn et al., "Blunted feedback suppression of SREBP processing by dietary cholesterol in transgenic mice expressing sterol–resistant SCAP(D443N)," *J. Clin. Invest.* 102(12):2050–2060 (Dec. 1998).
Lange et al., "Four cholesterol–sensing proteins," *Curr. Opin. Struct. Biol.* 8(4):435–439 (Aug. 1998).

Liu et al., "Oncostatin M activates low density lipoprotein receptor gene transcription in sterol–repressed liver Cells," *Cell Growth & Differentiation* 5:1333–1338 (Dec. 1994).
Liu et al., "Novel mechanism of transcriptional activation of hepatic LDL receptor by oncostatin M," *Journal of Lipid Research* 38:2035–2048 (1997).
Meier, "Regulation of cholesterol synthesis: of SCAP, SREBP, CBP and more," *Eur. J. Endocrinol* 136(3):271–272 (Mar. 1997).
Osbourne, "Cholesterol homeostasis: Clipping out a slippery regulator," *Current Biology* 7:R172–R174 (1997).
Thompson et al., "Novel lipid–regulating drugs," *Expert Opin. Investig. Drugs* 9(11):2619–2628 (2000).
Wang et al., "Nuclear protein that binds sterol regulatory element of low density lipoprotein receptor promoter," *The Journal of Biological Chemistry* 268(19):14497–14504 (Jul. 1993).
Nohturfft Axel et al: "Sterols regulate processing of carbohydrate chains of wild–type SREBP cleavage–activating protein (SCAP), but not sterol–resistant mutants Y298C or D44N", Proceedings of the National Academy of Sciences of the United States, vol. 95, No. 22, Oct. 27, 1998, pp. 12848–12853.
Nohturfft Axel et al: "Topology of SREBP cleavage–activating protein, a polytopic membrane protein with a sterol–sensing domain", Journal of Biological Chemistry, vol. 273, No. 27, Jul. 3, 1998, pp. 17243–17250.
Fajas Lluis et al: "Regulation of Peroxisome Proliferator–Activated Receptor γ Expression by Adipocyte Differentiation and Determination Factor 1/Sterol Regulatory Element Binding Protein 1: Implications for Adipocyte Differentiation and Metabolism", Molecular adn Cellular Biology, 1999, vol. 19, No. 8, pp. 5495–5503.
A. Simon et al., Circulation, vol. 96, 1997, pp. 2449–2452.
A.S. Brown et al., J. Am. Coll. Cardiol., vol. 32, 1998, pp. 665–672.
Cell, vol. 89, 1997, pp. 331–340.
M.R. Briggs et al., J. Biol. Chem., vol. 268, 1993, pp. 14490–14496.
C. Yokoyama et al., Cell, vol. 75, 1993, pp. 187–197.
X. Hua et al., Proc. Natil. Acad. Sci., vol. 90, 1993, pp. 11603–11607.

(List continued on next page.)

*Primary Examiner*—Gary Kunz
*Assistant Examiner*—Jegatheesan Seharaseyon
(74) *Attorney, Agent, or Firm*—Virginia C. Bennett

(57) ABSTRACT

The invention relates to a method for screening therapeutic agents, defined as SCAP antagonists, for use in combating diseases associated with elevated lipid levels, said method comprising detecting or assaying the extent or result of transcriptional activity or binding between a control SCAP antagonist and SCAP, in the presence of and absence of said agent. Also claimed are therapeuic agents which are antagonists of SCAP, identified by such a method and their use in combating diseases associated with elevated lipid levels.

19 Claims, 7 Drawing Sheets

OTHER PUBLICATIONS

J. Sakai et al., Mol. Cell, vol. 2, 1998, pp. 505–514.
R.B. Rawson et al., Mol. Cell, vol. 1, 1997, pp. 47–57.
J. Sakai et al., Cell, Vol. 85, 1996, pp. 1037–1046.
J. Sakai et al., J. Biol. Chem., vol. 272, 1997, pp. 20213–20221.
X. Hua et al., Cell, vol. 87, 1996, pp. 415–426.
N.B. Javitt, Faseb, vol. 9, 1995, p. 1378–1381.
M.S. Brown and J.L. Goldstein, J. Biol. Chem., vol. 249, 1974, pp. 7306–7314.
A. Nohthufft et al., Proc. Natl. Acad. Sci., vol. 93, 1996, pp. 13709–13714.

Control

25OH-cholesterol

Example 1

SEQUENCE LISTING

```
<160> NUMBER OF SEQ ID NOS: 14

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 1
ccctgactga aaggctgcgt gagaa                                            25

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 2
catagcgtgc tggccttccc aca                                              23

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 3
gaagatctca caaaacaaaa aatatttttt tggc                                  34

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Primer
```

```
<400> SEQUENCE: 4
ggccccatgg tcgcagcctc tgcccaggca gtgtcc                                    36

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
caattgttcc aggaaccagg                                                      20

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 6
ggggtaccaa tcagagcttc acgggttaaa a                                         31

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 7
ggggtaccac atcggccgtt cgaaactc                                             28

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 8
ggggtacctg aaaatcaccc cactgcaaac t                                         31

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
ggggtaccaa actcctcccc ctgctagaaa                                           30

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 10
ggggtacctc acattgaaat gctgtaaatg a                                         31

<210> SEQ ID NO 11
<211> LENGTH: 38
```

```
<212> TYPE: DNA
<213> ORGANISM: Artificial Sequence
<220> FEATURE:
<223> OTHER INFORMATION: Description of Artificial Sequence: Primer

<400> SEQUENCE: 11
gatctaaaat caccccactg caaaatcacc ccactgca                        38

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 12
aagacacatg cgacaggaat gag                                        23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13
gacccacttg ctggcgatac                                            20

<210> SEQ ID NO 14
<211> LENGTH: 16
<212> TYPE: DNA
<213> ORGANISM: Unknown Sequence
<220> FEATURE:
<223> OTHER INFORMATION: Description of Unknown Sequence:
      Oligonucleotide

<400> SEQUENCE: 14
aaaatcaccc cactgc                                                16
```

METHODS OF USING SCAP ANTAGONISTS

FIELD OF THE INVENTION

This application claims priority to Great Britain Application No. GB 9916757.9 filed Jul. 17, 1999.

The present invention relates to the novel use of the SREBP-cleavage activating protein (SCAP) in a screening method, particularly a method of screening for agents which compete for binding on SCAP, and to agents having SCAP binding characteristics for use in combating diseases associated with elevated lipid levels.

BACKGROUND

Cholesterol is transported in the blood in the form of protein/lipid complexes termed lipoproteins. Each lipoprotein plays a role in the transport of lipid from peripheral tissues to the liver or vice versa. Prolonged elevation of some of these classes of lipoproteins can lead to deposition of cholesterol and cholesterol esters in the arteries which may in turn lead to arterial occlusion and clinical conditions such as myocardial infarction and heart failure.

Numerous studies have shown a correlation between extent of atherosclerosis and the incidence of myocardial infarction and plasma level of low density lipoprotein (reviewed by Simon A et al., *Circulation* 96:2449–2452 (1997)). During the past decade, several clinical trials using inhibitors of HMGCoA-reductase, the rate limiting enzyme of cholesterol synthesis, have confirmed the beneficial effect of decreasing plasma LDL levels on cardiovascular mortality (Brown A. S. et al., *J. Am. Coll. Cardiol.* 32:665–672 (1998). The mechanism by which cholesterol depletion in hepatic cells prevents the down regulation of the LDL receptor, which mediates LDL re-uptake, has been well characterised by Brown and Goldstein (reviewed in *Cell* 89:331–340 (1997)). They have identified a responsive element in the LDL-receptor promoter which is involved in LDL-receptor regulation by sterols, the Sterol Responsive Element (SRE) (Briggs M. R. et al., *J. Biol. Chem.* 268:14490–14496 (1993)). They have purified and cloned two SRE binding proteins (SREBPs) present as precursor forms in the endoplasmic reticulum membrane (Yokoyama C. et al., *Cell* 75:187–197 (1993) and Hua X. et al., *Proc. Natl. Acad. Sci.* 90:11603–11607 (1993). Upon cholesterol depletion, these membrane bound forms are sequentially cleaved by two recently cloned proteases, S-1-P (Sakai J et al, *Mol. Cell*, 2:505–514 (1998)), and S-2-P (Rawson R. B. et al, *Mol. Cell*, 1:47–57 (1997)), and the mature forms thus released, migrate to the nucleus and bind to SRE (Sakai J. et al, *Cell* 85:1037–1046 (1996). The SREBP-cleavage activating protein (SCAP) has been identified and shown to interact physically with SREBPs (Sakai J. et al., *J. Biol. Chem.* 272:20213–20221 (1997). The presence of a putative sterol binding domain on SCAP between amino acid 280 to 444 further suggests its role is that of a "cholesterol sensor" (Hua X. et al.; *Cell* 87:415–426 (1996)). Excess cholesterol in the cell, presumably prevents the SCAP/SREBP interaction, thus blocking the SREBP proteolytic maturation process. Cholesterol and its metabolites act as repressors of genes that increase cellular cholesterol content e.g. those catalysing de novo cholesterol synthesis or mediating uptake of cholesterol-rich LDL (Javitt N. B., *Faseb* 9:1378–1381 (1995)). The water-soluble cholesterol analogue 25OH-cholesterol is a potent suppressor of sterol-regulated genes (Brown M. S. and Goldstein J. L., *J. Biol. Chem.*, 249:7306–7314 (1974)) and has been used to study SCAP function (Nohturfft A. et al., *Proc. Natl. Acad. Sci.* 93:13709–13714 (1996)).

SUMMARY OF THE INVENTION

A first aspect of the invention is a method for screening for a SCAP antagonist for use in combating diseases associated with circulating elevated levels of LDL-cholesterol, said method comprising detecting or assaying the extent or result of transcriptional activity or binding competition on SCAP between a test SCAP antagonist and a control SCAP antagonist, or between a test SCAP antagonist and cholesterol, or a metabolite thereof.

In an alternative or yet further aspect, there is provided a method for the treatment of conditions resulting from elevated circulating levels of LDL-cholesterol and/or triglycerides comprising administration of a SCAP antagonist.

DETAILED DESCRIPTION

Figure 1A:
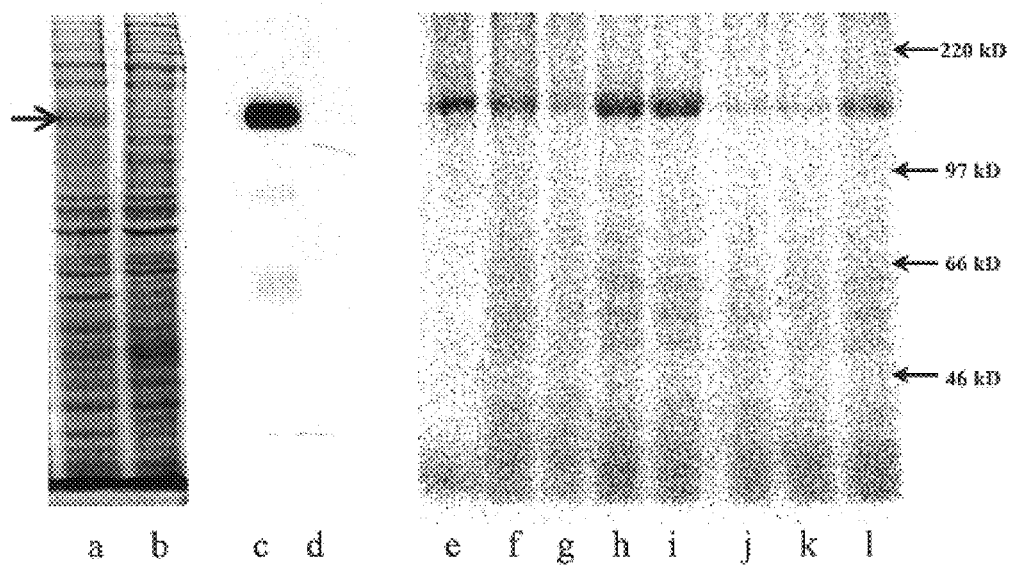
FIGS. 1A and 1B show the photo-affinity labeling of SCAP.

The inventors have now discovered agents which bind to SCAP in a way which has the opposite effect to cholesterol and its metabolites by promoting the activation of the SCAP/SREBP pathway (SCAP antagonists), thus leading to LDL-receptor gene activation. The fact that a SCAP antagonist could allow activation of the LDL-receptor promoter even in the presence of repressor sterol provides a definite advantage over drugs that act by depleting cellular cholesterol content, such as HMGCo-A reductase inhibitors (statins). The fact that repression of the LDL-receptor promoter by cholesterol and its metabolites remains possible in the presence of a SCAP antagonist shows that the use of a SCAP antagonist does not abolish the physiological regulation of the LDL-receptor.

Thus, according to a first aspect, the present invention provides a method for screening for a SCAP antagonist for use in combating diseases associated with elevated circulating levels of LDL-cholesterol, said method comprising detecting or assaying the extent or result of transcriptional activity or binding competition on SCAP between a test SCAP antagonist and a control SCAP antagonist, or between a test SCAP antagonist and cholesterol, or a metabolite thereof.

The methods of detection of binding according to the present invention comprise any suitable methods known in the art. Thus, a control SCAP antagonist may comprise a labelled compound, (i.e. one which is radioactive or fluorescent) and/or one which is photo-activable.

The present invention demonstrates that a SCAP antagonist which binds to SCAP can antagonise the repression by cholesterol of genes regulated by SREBPs such as the LDL receptor. Moreover, this new pharmacological class of compounds can act even in the presence of excess cholesterol and is potentially more potent than the other lipid lowering agents, such as statins, due to the fact that there is less chance of adaptive hepatic responses to counter the agents action. The effects of statins are limited by the degree to which inhibition of the cellular production of cholesterol and key intermediates in that process may take place without inducing cell damage. A hypolipemic drug that acts through competition with the endogenous ligands of SCAP does not require cholesterol depletion. The significant reduction of LDL-cholesterol, triglycerides and apoB100 observed in the cholesterol-fed hamster, as described in the examples hereinafter, confirms the therapeutic interest of SCAP ligands for the treatment of conditions associated with elevated circulating levels of LDL-cholesterol, particularly severe dyslipidemia. The significant reduction in plasma triglyceride levels observed on treatment with these agents is probably derived through enhanced clearance of triglyceride rich lipoproteins by LDL-receptor.

As used herein, the term 'screening' includes any method or assay whereby the action of an agent (test SCAP antagonist) capable of modulating, affecting, influencing or interfering with the binding between a control SCAP antagonist and SCAP or truncated forms of SCAP, or the transcriptional ability of cholesterol or one of its metabolites bound to SCAP is investigated, and includes binding assays in which a single agent or compound is investigated as well as assays in which more than one compound, such as an array of compounds, or a library of compounds is tested. In the case of testing more than one agent, these tests may be either simultaneous or sequential. Such agents may act to interfere with the binding of cholesterol or its metabolites to SCAP, i.e. to prevent, wholly or partially, the binding of cholesterol or its metabolites on SCAP. Such agents may act also to modulate the transcriptionally repressive activity of cholesterol or its metabolites bound to SCAP, i.e. to inhibit the transcriptional repression mediated by SCAP when bound to cholesterol or its metabolites and thereby promoting the activation of the SREBP pathway and LDL-receptor gene activation. The methods of detection and assay include any quantitative, qualitative or semiquantitative assessment of whether there is any binding or transcriptional activity, and of the effect of the agent being tested.

In one aspect, the present invention involves a binding assay whereby the binding between SCAP and a labelled control SCAP antagonist, in the presence of a test SCAP antagonist, with that in the absence of said test SCAP antagonist, is compared.

In a second aspect, the present invention involves a functional assay whereby the extent of activation of the SREBP pathway is determined in the presence of a test SCAP antagonist, and then confirming that the effect is mediated by antagonising the effect of cholesterol bound to SCAP by comparing the binding between a labelled control SCAP antagonist and SCAP in the presence of said test SCAP antagonist, with that in the absence of said test SCAP antagonist. A preferred functional assay according to the invention comprises determination of the extent of transcriptional activation of the LDL-receptor promoter in HepG2 cells.

SCAP antagonists of the invention are of use in the treatment of atherosclerosis, pancreatitis, non-insulin dependent diabetes mellitus (NIDDM), coronary heart diseases and obesity.

SCAP antagonists of the invention are also useful in lowering serum lipid levels, cholesterol and/or triglycerides, and are of use in the treatment of hyperlipemia, hyperlipidemia, hyperlipoproteinemia, hypercholesterolemia and/or hypertriglyceridemia. SCAP antagonists of the further aspects of the invention are most useful in treating hypercholesterolemia and mixed dyslipidemia.

Thus, viewed from a further aspect, the present invention provides a therapeutic agent (SCAP antagonist), or a physiologically acceptable salt, solvate or derivative thereof, identified by the aforementioned screening method according to the present invention, and its use in combating diseases associated with elevated circulating levels of LDL-cholesterol and/or triglycerides.

Suitable SCAP antagonists according to the invention include 4-(4-chloro-benzoylamino)-N-{4-[4-(2-ethoxy-4-ethyl-phenyl)-piperidin-1-yl]-butyl}-benzamide or 4-(4-benzoyl)-N-{4-[4-(4-isopropyl-2-methoxy-phenyl)-piperidin-1-yl]-butyl}-benzamide, or a physiologically acceptable salt, solvate or derivative thereof.

Preferred SCAP antagonists according to the invention include 4'-chloro-biphenyl-4-carboxylic acid {4-[4-(1-methoxy-naphtalen-2-yl)-piperidin-1-yl]-butyl}-amide, or a physiologically acceptable salt, solvate or derivative thereof.

The invention provides, as a further aspect, the use of a SCAP antagonist, or a physiologically acceptable salt, solvate or derivative thereof, in the manufacture of a medicament for use in the treatment of conditions resulting from elevated circulating levels of LDL-cholesterol and/or triglycerides.

In an alternative or further aspect, there is provided a method for the treatment of a mammal, including man, in particular in the treatment of conditions resulting from elevated circulating levels of LDL-cholesterol and/or triglycerides, comprising administration of an effective amount of a SCAP antagonist, or a physiologically acceptable salt, solvate or derivative thereof.

In a further alternative or yet further aspect, there is provided a method for identifying compounds which will be useful in for the treatment of conditions resulting from elevated circulating levels of LDL-cholesterol and/or triglycerides comprising the step of determining whether the compound interacts directly with SCAP.

In a further alternative or yet further aspect, there is provided a method for the treatment of conditions resulting from elevated circulating levels of LDL-cholesterol and/or triglycerides comprising administration of a compound which may be identified by the aforementioned method.

It will be appreciated that reference to treatment is intended to include prophylaxis as well as the alleviation of established symptoms. Compounds of formula (I) may be administered as the raw chemical but the active ingredient is preferably presented as a pharmaceutical formulation.

Accordingly, the invention also provides a pharmaceutical composition which comprises at least one SCAP antagonist, or a physiologically acceptable salt, solvate or derivative thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus, compounds of formula (I) may be formulated for oral, buccal, parenteral, transdermal, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or lozenges formulated in conventional manner.

For transdermal administration the compounds according to the invention may be formulated as creams, gels, ointments or lotions or as a transdermal patch. Such compositions may for example be formulated with an aqueous or oily base with the addition of suitable thickening, gelling, emulsifying, stabilising, dispersing, suspending, and/or colouring agents.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unit dose device or alternatively as a powder mix with a suitable carrier for administration using a suitable delivery device.

The compositions may contain from 0.1% upwards, e.g. 0.1–99% of the active material, depending on the method of administration. A proposed dose of the compounds of the invention is 0.25 mg/kg to about 125 mg/kg bodyweight per day e.g. 20 mg/kg to 100 mg/kg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

SCAP antagonists according to the invention may, if desired, be administered with one or more therapeutic agents and formulated for administration by any convenient route in a conventional manner. Appropriate doses will be readily appreciated by those skilled in the art. For example, SCAP antagonists according to the invention may be administered in combination with other lipid lowering drugs acting through cholesterol depletion or by reducing VLDL production, for instance inhibition of enzymes involved in cholesterol biosynthesis such as an HMGCo-A reductase inhibitor, or a microsomal triglyceride transfer protein (MTP) inhibitor and/or a bile acid sequestrant or bile acid transporter inhibitor.

Figure 1B:
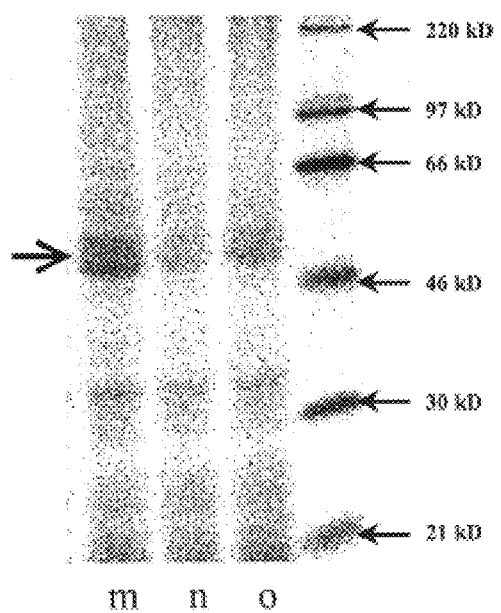
Figure 2:
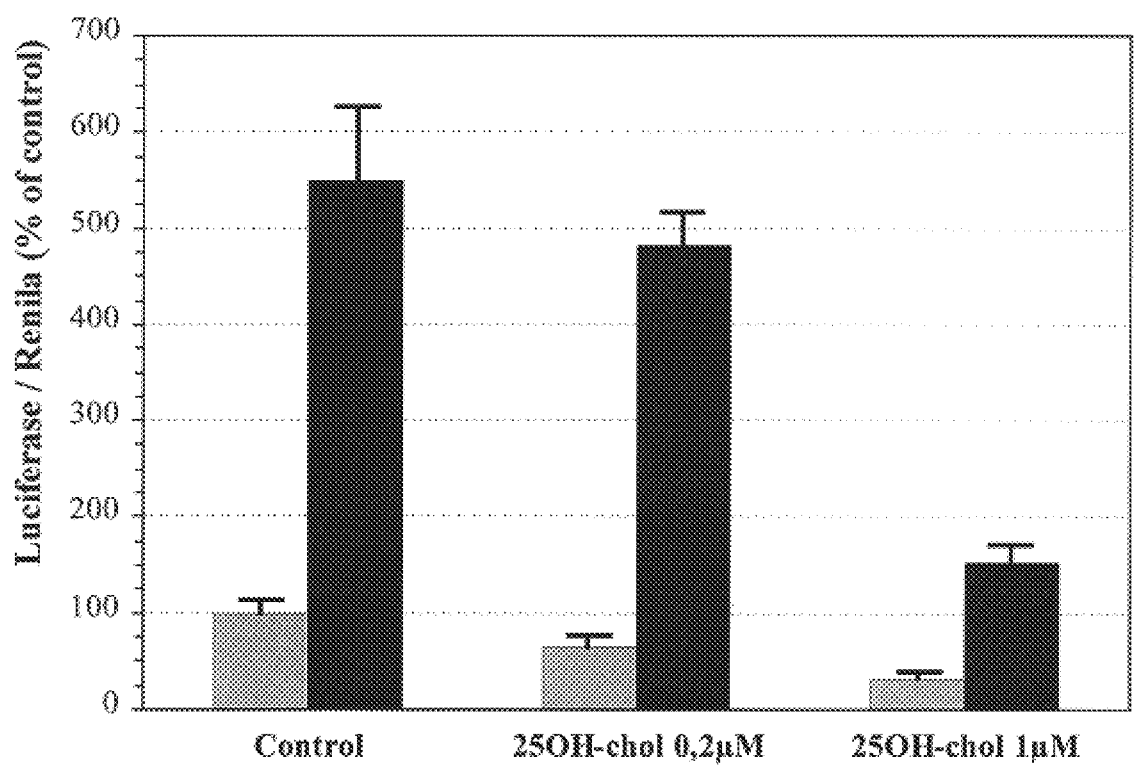
FIG. 2 shows LDL-receptor promoter activation and competition of SCAP antagonist with 25OH-cholesterol.
Figure 3A:
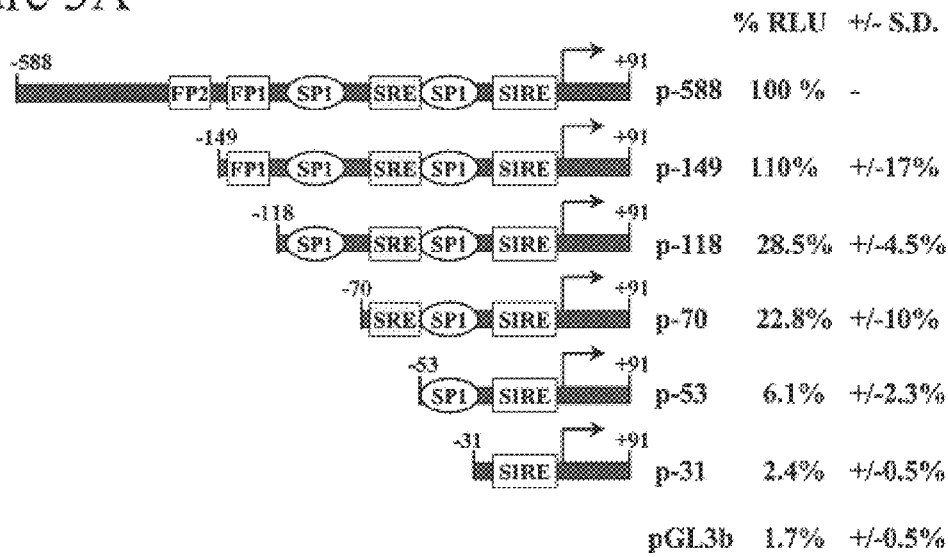
FIG. 3A shows the shortened LDL-receptor promoter constructs.
Figure 3B:
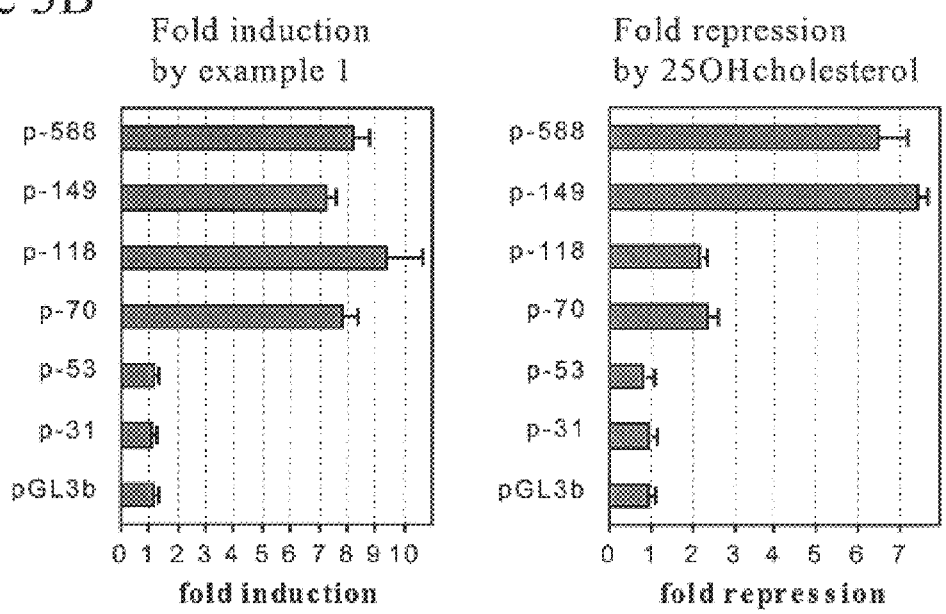
FIG. 3B graphs the reporter gene expression in HepG2 cells exposed to the compound of Example 1 or 25OH cholesterol.
Figure 3C:
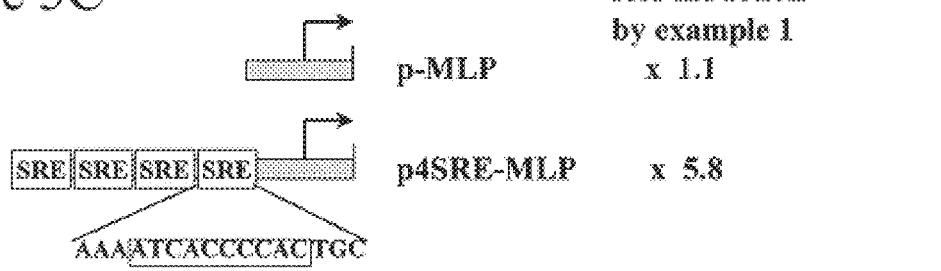
FIG. 3C indicates the use of a promoter construct containing four Sterol Responsive Elements.
Figure 4:
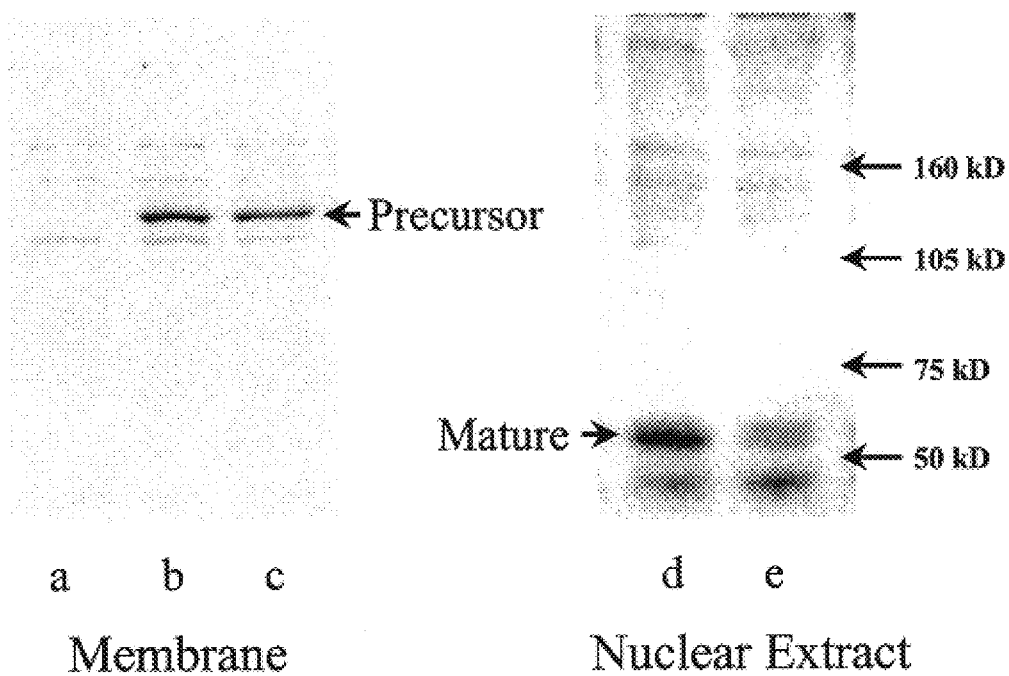
FIG. 4 shows western blot results from HepG2 cells encoding human SREBP-2 treated with the compound of Example 1.
Figure 5A:
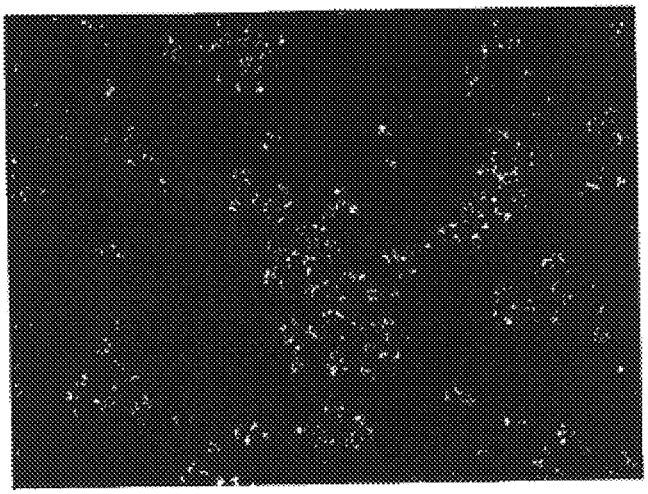
FIG. 5A shows the uptake of Dil-LDL by HepG2 cells (control).
Figure 5B:
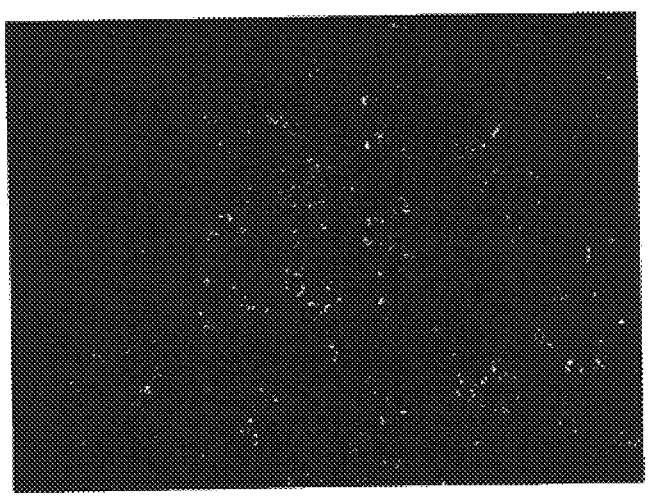
FIG. 5B shows the uptake of Dil-LDL by HepG2 cells exposed to 25OH-cholesterol.
Figure 5C:
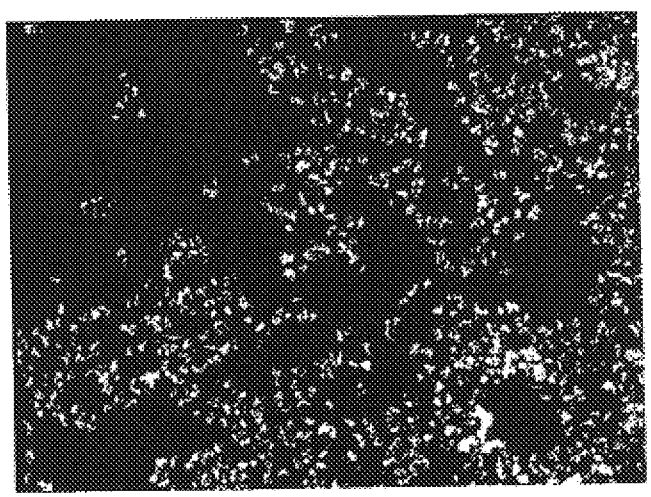
FIG. 5C shows the uptake of Dil-LDL by HepG2 cells exposed to the compound of Example 1.
Figure 6:
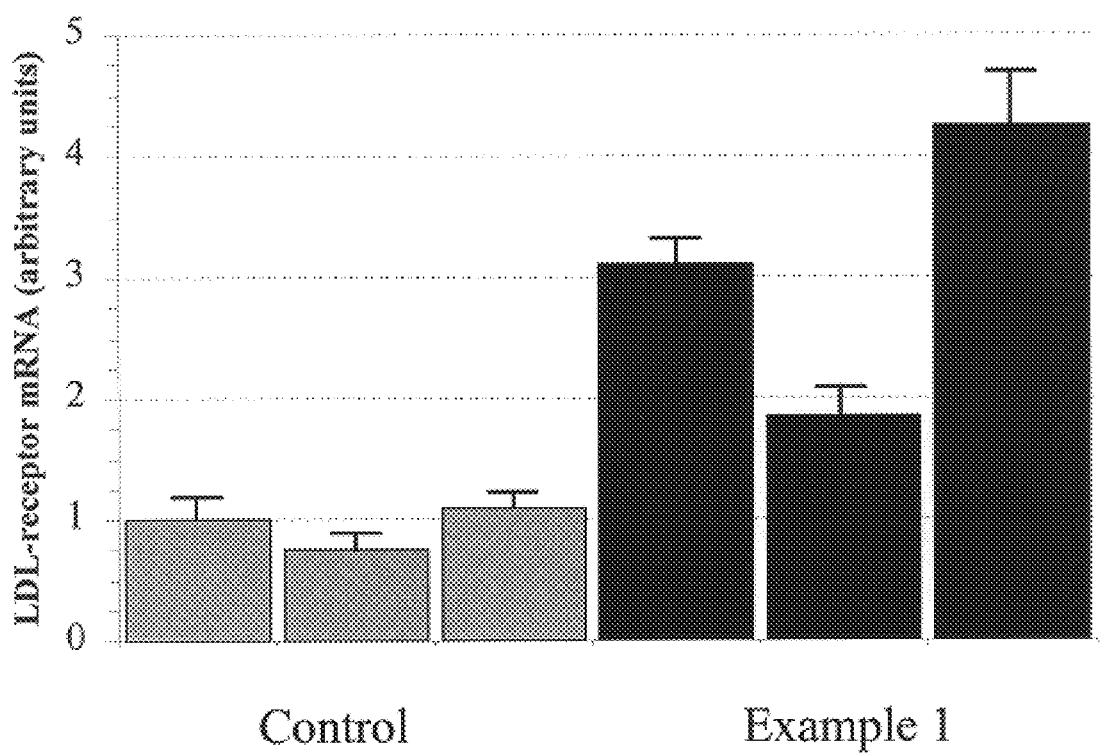
FIG. 6 shows that SCAP antagonist increases the mRNA of LDL-receptor in the liver of fat-fed hamsters.
Figure 7:
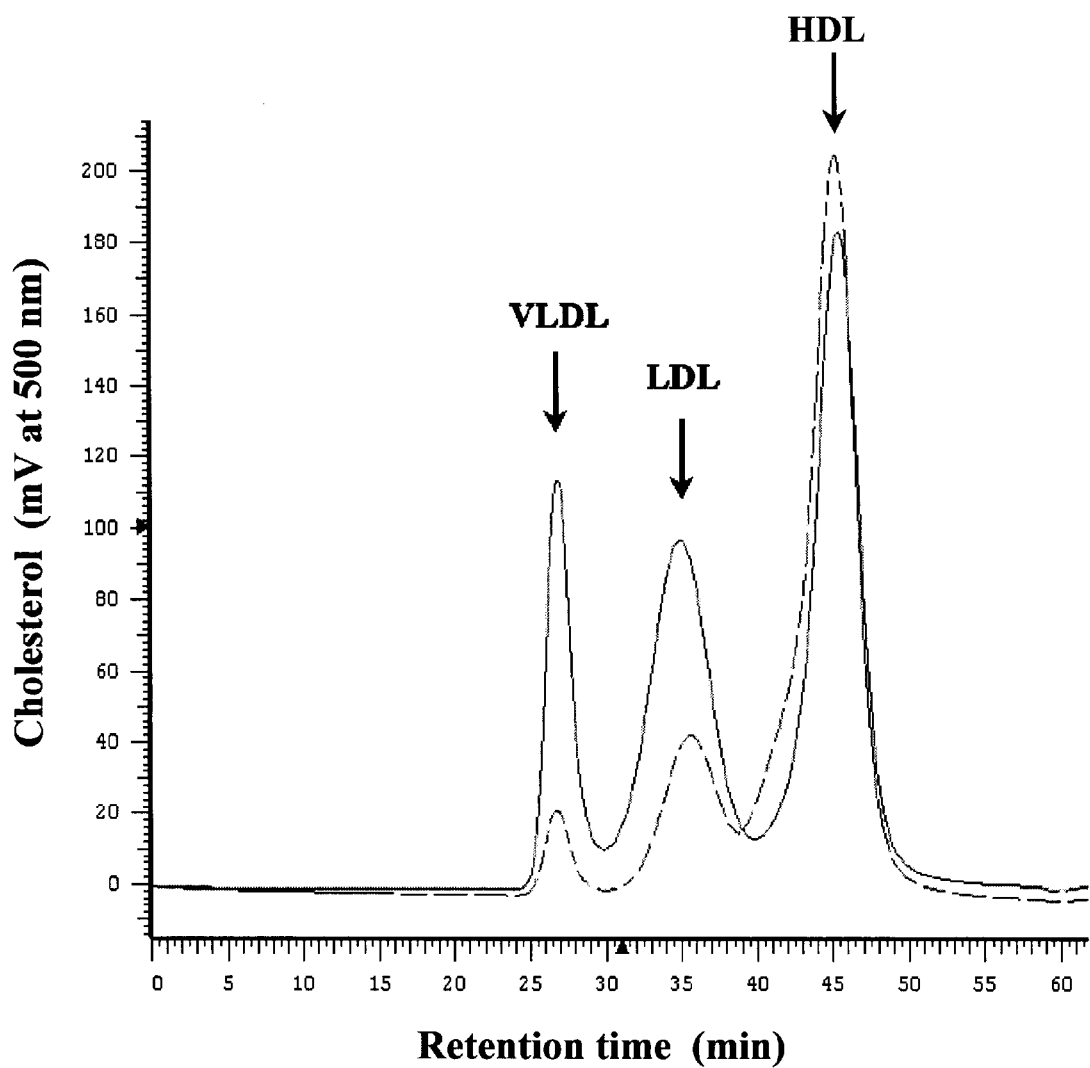
FIG. 7 shows that SCAP antagonist decreases cholesterol associated with circulating LDL and VLDL in fat-fed hamsters.

The invention will now be described with reference to the following non-limiting examples in which:

FIG. 1 and FIG. 2 shows the photo-affinity labeling of SCAP;

FIG. 2 shows LDL-receptor promoter activation and competition of SCAP antagonist with 25OH-cholesterol;

FIGS. 3A, 3B, 3C shows that the SRE present in LDL-receptor promoter is responsible for the effect of SCAP antagonist;

FIG. 4 shows that SCAP antagonist induces the proteolytic maturation of SREBP-2 in HepG2 cells;

FIG. 5 shows the uptake of Dil-LDL by HepG2 cells;

FIG. 6 shows that SCAP antagonist increases the mRNA of LDL-receptor in the liver of fat-fed Hamsters and FIG. 7 shows that SCAP antagonist decreases cholesterol associated with circulating LDL and VLDL in fat-fed hamsters

EXAMPLES

Preparation of Test and Control SCAP Antagonists

Abbreviations used in the following experimental details: THF-Tetrahydrofuran; DCM-Dichloromethane; TEA-triethylamine; NaOH-Sodium hydroxyde; EtOH-Ethanol; EtOAc-Ethyl acetate; IPr$_2$O-Isopropanol Me$_2$NH-Dimethylamine; Na$_2$SO$_4$-Sodium sulfate; Pd/C-Palladium on carbon; Cs$_2$CO$_3$-Cesium carbonate; Et$_2$O-Diethyl ether; CHCl$_3$-Chloroform; IPrOH-Isopropanol; Chex-cyclohexane; MeOH-Methanol; K$_2$CO$_3$; Potassium carbonate; DMF-Dimethylformamide; EDCl-1-(3-dimethylaminopropyl)-3-ethylcarbodiimide hydrochloride; HOBt-1-Hydroxybenzotriazole; pTSA-Para toluene sulfonic acid; NaHCO$_3$-Sodium hydrogeno carbonate; LiAlH$_4$-Lithium aluminium hydride; rt-Room temperature

4-(4-Chloro-benzoylamino)-benzoic Acid Ethyl Ester

Intermediate 1

A solution of 4-Amino-benzoic acid ethyl ester (124 g, 0.75 mol) in THF/DCM (500 mL/1000 mL) was treated with TEA (120 mL, 1.15 eq.) and 4-Dimethylaminopyridine (1.3 g, catalytic amount). At −7° C. a solution of 4-Chloro-benzoyl chloride (152.0 g, 1.15 eq.) in THF (100 mL) was added dropwise. The resulting mixture was stirred mechanically for 48 hours. The solvent was evaporated off and the residue was taken up in EtOAc/DCM (30/70). Concentrated NaOH solution was added until pH=12. A white solid precipitated out and was collected (156.8 g, 0.52 mol). The organic layer was dried over Na$_2$SO$_4$. The solvent was evaporated off and crystallisation from iPr$_2$O gave a second batch of the desired compound (63.2 g, 0.21 mol). The overall yield is 97.3%.

$^1$H NMR (CDCl$_3$, 250 MHz) δ 8.1 (s, 1H), 7.9 (d, 2H), 7.7 (d, 2H), 7.6 (d, 2H), 7.3 (d, 2H), 4.3 (q, 2H), 1.3 (t, 3H).

4-(4-Chloro-benzoylamino)-benzoic Acid

Intermediate 2

A suspension of intermediate 1 (220 g, 0.72 mol) in 4000 mL of EtOH was treated with a 1N NaOH solution (1000 mL). The resulting suspension was heated at reflux overnight. A white solid precipitated out. At reflux, concentrated HCl solution was added until pH=1. Under rigorous mechanical stirring, the resulting suspension was cooled down. A white solid was collected and dried under reduced pressure to give the title compound in a quantitative yield.

MP>260° C. $^1$H NMR (DMSO, 250 MHz) δ 10.5 (s, 1H), 7.9 (d, 2H), 7.8 (s, 4H), 7.5 (d, 2H). Ref: J. Pharm. Sci. (1979), 68(3), 332–5.

5-Ethyl-2-(1,2,3,6-tetrahydro-pyridin-4-yl)-phenol

Intermediate 3

A solution of 3-Ethyl-phenol (122.2, 1 mol) and 4-Piperidone hydrate hydrochloride (184.2 g 1.2 eq.) in acetic acid (500 mL) was treated with HCl gaz for 10 min. The mixture was stirred at 95° C. for 30 min. After cooling to rt, the mixture was treated again with HCl gaz for 5 min. The resulting solution was allowed to stir at rt for 4 days. The solvent was evaporated under reduced pressure to give the a colorless oil (200.0 g). The product was used without further purification.

Acetic Acid 2-(1-Acetyl-1,2,3,6-tetrahydro-pyridin-4-yl)-5-ethyl-phenyl Ester

Intermediate 4

To a solution of intermediate 3 (33.0 g, 0.162 mol) in pyridine (300 mL) was added acetic anhydride (100 mL). The mixture was stirred at rt for 4 hours. The solvents were evaporated under reduce pressure. The oil was diluted with DCM and washed with water. The organic layer was dried over Na$_2$SO$_4$ and evaporated to dryness to give the title compound (28.0 g, 0.097 mol) as a yellow oil in a 60% yield.

$^1$H NMR (CDCl$_3$, 250 MHz) δ 7 (m, 2H), 6.7 (m, 1H), 5.65 (m, 1H), 4.05 (m, 2H), 3.55 (dt, 2H), 2.6 (q, 2H), 2.3 (m, 2H), 2.15 (s, 3H), 2.05 (d, 3H), 1.1 (t, 3H).

1-[4-(4-Ethyl-2-hydroxy-phenyl)-3,6-dihydro-2H-pyridin-1-yl]-ethanone

Intermediate 5

To a solution of intermediate 4 (28.0 g, 0.098 mol) in MeOH (700 mL) was added K$_2$CO$_3$ (40.0 g, 3 eq.) and the mixture was stirred under reflux for 4 hours. The solution was filtered off and the methanol was evaporated. The oil was diluted with DCM and washed with water. The organic layer was dried over Na$_2$SO$_4$ and evaporated to dryness to give the title compound (20.0 g, 0.082 mol) as a orange oil in a 84% yield.

$^1$H NMR (CDCl$_3$, 250 MHz) δ 6.7 (m, 2H), 6.6 (m, 1H), 5.8 (m, 1H), 4.1 (m, 2H), 3.65 (m, 2H), 2.7 (m, 5H), 2.4 (q, 2H), 1.2 (t, 3H).

1-[4-(4-Ethyl-2-hydroxy-phenyl)-piperidin-1-yl]-ethanone

Intermediate 6

To a solution of intermediate 5 (20.0 g, 0.082 mol) in MeOH (600 mL) was added Pd/C, 10% (1.2 g) and the reaction was stirred under an atmospheric pressure of hydrogen for 24 hours. The reaction mixture was filtered through a bed of celite. The filtrate was evaporated under reduced pressure to give the title compound (15.0 g, 0.06 mol) as an oil in a 75% yield.

$^1$H NMR (CDCl$_3$, 250 MHz) δ 6.85 (d, 1H), 6.6 (m, 2H), 4.65 (m, 1H), 3.8 (m, 1H), 3.2–2.9 (m, 2H), 2.6 (m, 1H), 2.45 (q, 2H), 2.05 (s, 3H), 1.7 (m, 2H), 2H), 1.5 (m, 2H), 1.1 (t, 3H).

1-[4-(2-Ethoxy-4-ethyl-phenyl)-piperidin-1-yl]-ethanone

Intermediate 7

To a solution of intermediate 6 (7.41 g, 0.03 mol) in dry acetone (150 mL) was added anhydrous Cs$_2$CO$_3$ (14.7 g, 1.5 eq.) and ethyl iodide (4.8 mL, 2 eq.). The reaction was stirred under reflux for 5 hours. After cooling, the reaction was filtered off and washed with acetone. The filtrate was evaporated under reduced pressure to give the title compound as an oil (8.2 g, 0.03 mol) in a quantitative yield.

$^1$H NMR (CDCl$_3$, 250 MHz) δ 6.9 (d, 1H), 6.6 (m, 2H), 4.7 (m, 1H), 4.0 (q, 2H) 3.8 (m, 1H), 3.1 (m, 2H), 2.5 (m, 3H), 2.05 (s, 3H), 1.7(m, 2H), 1.50 (m, 2H), 1.35 (t, 3H), 1.1 (t, 3H).

4-(2-Ethoxy-4-ethyl-phenyl)-piperidine

Intermediate 8

To a solution of intermediate 7 (8.17 g, 0.03 mol) in MeOH (150 mL) was added a solution of NaOH (37 mL) in $H_2O$ (37 mL). The reaction was stirred under reflux for 16 hours. After cooling, the reaction was concentrated under reduced pressure, was diluted with DCM and washed with water. The organic layer was dried over $Na_2SO_4$ and evaporated to dryness to give the title compound (6.6 g, 0.028 mol) as a yellow oil in a 94% yield.

$^1$H NMR (CDCl$_3$, 250 MHz) δ 7.1 (d, 1H), 6.7 (d, 1H), 4.7 (d, 1H), 4.05 (q, 2H) 3.1 (m, 2H), 3.05 (m, 1H), 2.7 (td, 2H), 2.55 (q, 2H), 1.75 (m, 3H), 1.55 (m, 2H), 1.35 (t, 3H), 1.1 (t, 3H).

2-{4-[4-(2-Ethoxy-4-ethyl-phenyl)-piperidin-1-yl]-butyl}-isoindole-1,3-dione

Intermediate 9

A solution of intermediate 8 (6.6 g, 0.028 mol) in acetone (200 mL) was treated with $Cs_2CO_3$ (1.1 eq.) and N-(4-Bromobutyl)-phtalimide (1.1 eq.). The resulting mixture was stirred at reflux for 16 hours. After cooling to rt the reaction mixture was filtered off. The cake was washed with acetone. The filtrate was evaporated off to give the title compound (11.9 g, 0.027 mol) as a yellow oil in a 97% yield.

$^1$H NMR (CDCl$_3$, 250 MHz) δ 7.8 (m, 2H), 7.6 (m, 2H), 7.0 (d, 1H), 6.65 (dd, 1H), 6.55 (sd, 1H), 3.95 (q, 2H), 3.65 (m, 3H), 2.95 (m, 2H), 2.8 (m, 1H), 2.5 (q, 2H), 2.4 (m, 2H), 2 (td, 2H), 1.8–1.4 (m, 8H), 1.3 (t, 3H), 1.15 (t, 3H).

4-[4-(2-Ethoxy-4-ethyl-phenyl)-piperidin-1-yl]-butylamine

Intermediate 10

A solution of intermediate 9 (11.9 g, 0.027 mol) in MeOH (300 mL) was treated with hydrazine (4 eq.). The resulting mixture was stirred at 60° C. for 16 hours. After cooling to rt, a 1N HCl solution was added until pH=4. After evaporation under reduced pressure the residue was taken up in water. Filtration gave a yellow solution that was treated with an aqueous solution of $K_2CO_3$. Extraction with DCM/MeOH (90/10), drying over $Na_2SO_4$ and filtration gave the title compound (6.8 g, 0.022 mol) as a yellow oil in a 81.5% yield.

$^1$H NMR (CDCl$_3$, 250 MHz) δ 7.1 (d, 1H), 6.7 (dd, 1H), 6.6 (s, 1H), 4.0 (q, 2H), 3.0 (bd, 2H), 2.9 (m, 1H), 2.7 (t, 2H), 2.55 (q, 2H), 2.3 (m, 2H), 2.0 (td, 2H), 1.7–1.2 (m, 10H), 1.4 (t, 3H), 1.1 (t, 3H).

5-Isopropyl-2-(1,2,3,6-tetrahydro-pyridin-4-yl)-phenol

Intermediate 11

A solution of 3-Isopropyl-phenol (68.1 g 0.5 mol) and 4-Piperidone hydrate hydrochloride (92.1 g, 1.2 eq.) in acetic acid (300 mL) was treated with HCl gaz for 10 min. The mixture was stirred at 95° C. for 30 min. After cooling to rt, the mixture was treated again with HCl gas for 5 min. The resulting solution was allowed to stir at rt for 4 days. The solvent was evaporated under reduced pressure to give a colorless oil (110.0 g). The product was used without further purification.

Acetic Acid 2-(1-Acetyl-1,2,3,6-tetrahydro-pyridin-4-yl)-5-isopropyl-phenyl Ester Intermediate 12

To a solution of intermediate 11 (110.0 g, 0.5 mol) in pyridine (1000 mL) was added acetic anhydride (300 mL). The mixture was stirred at rt for 4 hours. The solvents were evaporated under reduce pressure. The oil was diluted with DCM and washed with water. The organic layer was dried over $Na_2SO_4$ and evaporated to dryness to give the title compound (150.0 g, 0.5 mol) as a yellow oil in a quantitative yield.

GC/MS: M+$C_{18}H_{23}NO_3$ 301.

1-[4-(2-Hydroxy-4-isopropyl-phenyl)-3,6-dihydro-2H-pyridin-1-yl]-ethanone

Intermediate 13

To a solution of intermediate 12 (150.0 g, 0.098 mol) in MeOH (700 mL) was added $K_2CO_3$ (40.0 g, 3 eq.) and the mixture was stirred under reflux for 4 hours. The solution was filtered and the methanol was evaporated. The oil was diluted with DCM and washed with water. The organic layer was dried over $Na_2SO_4$ and evaporated to dryness to give the title compound (76.0 g, 0.29 mol) as an orange oil in a 59% yield.

GC/MS: M+$C_{16}H_{21}NO_2$ 259.

1-[4-(2-Hydroxy-4-isopropyl-phenyl)-piperidin-1-yl]-ethanone

Intermediate 14

To a solution of intermediate 13 (56.0 g, 0.22 mol) in EtOH (1400 mL) was added Pd/C, 10% (5.6 g) and the reaction was stirred under an atmospheric pressure of hydrogen for 24 hours. The reaction mixture was filtered through a bed of celite. The filtrate was evaporated under reduced pressure to give the title compound (54.5 g, 0.21 mol) as an oil in a quantitative yield.

GC/MS: M+$C_{16}H_{23}NO_2$ 261.

1-[4-(4-Isopropyl-2-methoxy-phenyl)-piperidin-1-yl]-ethanone

Intermediate 15

To a solution of intermediate 14 (54.5 g, 0.21 mol) in dry acetone (1000 mL) was added anhydrous $K_2CO_3$ (43.0 g, 1.5 eq.) and methyl iodide (130 mL, 10 eq.). The reaction was stirred at 60° C. for 5 hours. After cooling, the reaction was filtered off and evaporated under reduced pressure. The oil was diluted with DCM and washed with water. The organic layer was dried over $Na_2SO_4$ and evaporated to dryness to give the title compound (55.7 g, 0.203 mol) as a yellow oil in a 96% yield.

GC/MS: M+$C_{17}H_{25}NO_2$ 275.

4-(4-Isopropyl-2-methoxy-phenyl)-piperidine

Intermediate 16

To a solution of intermediate 15 (55.7 g, 0.200 mol) in EtOH (500 mL) was added a solution of NaOH (270 mL) in $H_2O$ (270 mL). The reaction was stirred under reflux for 16 hours. After cooling, the reaction was concentrated under reduced pressure, was diluted with DCM and washed with water. The organic layer was dried over $Na_2SO_4$ and evaporated to dryness to give the title compound (48.8 g, 0.20 mol) as a yellow oil in a quantitative yield.

GC/MS: M+$C_{15}H_{23}NO$ 233.

2-{4-[4-(4-Isopropyl-2-methoxy-phenyl)-piperidin-1-yl]-butyl}-isoindole-1,3-dione Intermediate 17

The same method was employed as in the preparation of intermediate 9 but starting from intermediate 16 gave the title compound as a yellow oil in a quantitative yield.

$^1$H NMR (CDCl$_3$, 250 MHz) δ 7.8 (m, 2H), 7.65 (m, 2H), 7.05 (d, 1H), 6.7 (dd, 1H), 6.6 (s, 1H), 3.7 (s, 3H), 3.65 (m, 3H), 2.9 (m, 1H), 3.0 (bd, 2H), 2.8 (m, 2H), 2.3 (m, 2H), 2.0 (m, 2H), 1.70–1.5 (m, 6H), 1.2 (d, 6H).

4-[4-(4-Isopropyl-2-methoxy-phenyl)-piperidin-1-yl]-butylamine

Intermediate 18

The same method was employed as in the preparation of intermediate 10 but starting from intermediate 17 gave the title compound as an oil in a 93% yield.

$^1$H NMR (CDCl$_3$, 250 MHz) δ 7.05 (m, 1H), 6.7 (dd, 1H), 6.6 (d, 1H), 3.8 (s, 3H), 3.1 (bd, 2H), 2.8 (m, 2H), 2.7 (t, 2H), 2.3 (m, 2H), 2.0–1.3 (m, 12H), 1.15 (d, 6H).

17α,17β-(1,3,6,8-Tetraoxaspiro[4.4]nonan-4-yl)-3,11-dioxoandrost-4-ene

Intermediate 19

A solution of Cortisone (30.0 g, 0.083 mol) in CHCl$_3$ (1000 mL) was treated with concentrated HCl (300 mL) followed by formaldehyde (300 mL). The resulting mixture was stirred for 16 hours at rt. The organic layer was separated, washed with H$_2$O, a saturated NaHCO$_3$ solution and brine. The organic layer was dried over Na$_2$SO$_4$ and evaporated off. The title compound was precipitated from acetone as a white solid (15.04 g, 0.037 mol) in a 45% yield.

$^1$H NMR (CDCl$_3$, 250 MHz) δ 5.55 (s, 1H), 5.1 (s, 1H), 4.95 (d, 2H), 4.9 (s, 1H), 3.7 (s, 2H), 2.7–1.1 (m, 20H), 0.7 (s, 3H).

3-Ethoxy-androst-3,5-diene-17α,17β-(1,3,6,8-tetraoxaspiro[4.4]nonan-4-yl)-11-one

Intermediate 20

A solution of intermediate 19 (6.0 g, 0.015 mol) in 1,4-dioxane (150 mL) was treated with Triethyl orthoformate (4.96 mL, 2 eq.) and pTSA (0.142 g, 0.05 eq.). The reaction was stirred while it was followed by TLC (silica gel:Chex/EtOAc: 5/5). The resulting mixture was treated with pyridine (0.21 mL, 0.2 eq.) for 15 min at rt, followed by H$_2$O (20 mL). The reaction was then extracted with Et$_2$O. The organic layer was dried over Na$_2$SO$_4$ and evaporated off. The title compound was precipitated from acetone as a yellow solid (6.4 g, 0.015 mol) in a quantitative yield.

GC/MS: M+C$_{25}$H$_{34}$O$_6$ 430.

3-Ethoxy-androst-3,5-diene-17α,17β-(1,3,6,8-tetraoxaspiro[4.4]nonan-4-yl)-11-one-6-carboxaldehyde

Intermediate 21

To the DMF (3.93 mL, 3.2 eq.) in DCM (50 mL) was added the phosgene (20% in toluene solution, 13.4 mL, 2 eq.) The reaction was stirred and a white precipitate was formed. A solution of intermediate 20 (6.4 g, 0.015 mol) in DCM (50 mL) was added dropwise and the reaction was stirred for 3 hours and treated with a 2N Na$_2$CO$_3$ solution. The reaction was stirred for 15 min. and the product was extracted with DCM. The organic layer was washed with brine, dried over Na$_2$SO$_4$ and evaporated off to give the title compound as a white solid (6.75 g, 0.015 mol) in a quantitative yield.

MP: 90–91° C.; GC/MS: M+C$_{26}$H$_{34}$O$_7$ 458.

3-Ethoxy-6-dimethylaminomethyl-androst-3,5-diene-17α,17β-(1,3,6,8-tetraoxaspiro[4.4]nonan-4-yl)-11-one

Intermediate 22

A solution of Intermediate 21 (5.0 g, 0.011 mol) in dry THF (50 mL) was added the Me$_2$NH (2M in THF solution, 16.4 mL, 3 eq.) The reaction was stirred for 16 hours at rt and the sodium triacetoxyborohydride (2.54 g, 1.1 eq.) was added. The reaction was stirred for 1 hour and AcOEt (50 mL) was added. The organic layer was washed with H$_2$O, brine, dried over Na$_2$SO$_4$ and evaporated off. Purification by chromatography on silica gel (DCM/MeOH: 9/1) give the title compound as an oil (3.39 g, 0.007 mol) in a 63% yield.

GC/MS: M+C$_{28}$H$_{41}$NO$_6$ 487.

$^{14}$C-labelled 4-Cyanobenzophenone

Intermediate 23

4-Iodobenzophenone (3.0) (410 mg, 1.33 mmol), finely divided copper (I) iodide (40 mg, 0.21 mmol) and $^{14}$C-potassium cyanide (64 mg, 0.95 mmol, 56.2 mCi/mmol) were taken up in anhydrous DMF (2.5ml) and heated at reflux for 20 hours under nitrogen. The reaction mixture was cooled to room temperature before dilution with ethyl acetate (150 ml). The solution was extracted sequentially with 2% w/w ferric chloride (60 ml), water (50 ml), sodium metabisulphite (60 ml), water (50 ml), brine (50 ml) and finally water (50 ml). The organic layer was dried (sodium sulphate) and concentrated under reduced pressure to give an off white solid. The material was purified by silica column chromatography eluting initially with isohexane-dichloromethane (80:50) then increasing to (50:100) after elution of 4-iodobenzophenone (3.0), to give the title compound (3.1) as a white solid (194 mg, 97%). Co-elutes with authentic 4-cyanobenzophenone.

TLC (Merck 5714): isohexane-dichloromethane (80:50), R$_f$=0.1*. $^1$H NMR spectrum: (CDCl$_3$, 400MHz) 7.5 (t, 2H), 7.6 (t, 1H) 7.8 (m, 4H), 7.9 (d, 2H)*.

*Data for non-labelled compound

$^{14}$C-labelled 4-Benzoylbenzoic Acid

Intermediate 24

Intermediate 23 (194 mg, 0.92 mmol) was taken up in 2N sodium hydroxide (10 ml) and ethanol (2 ml) and the resulting mixture heated under reflux for 4 hours. The reaction mixture was allowed to cool to room temperature before acidification with 2N hydrochloric acid (15 ml). The precipitate was extracted into ethyl acetate (150 ml). The aqueous layer was removed and back washed with ethyl acetate (50 ml). The combined organics were dried (sodium sulphate) and concentrated under reduced pressure to give the title compound (3.2) as a pale yellow solid (211 mg, 100%). Co-elutes with authentic 4-benzoyl benzoic acid. TLC(Merck 5714): isohexane-ethyl acetate-acetic acid (60:20:1), R$_f$=0.3*.

$^1$H NMR spectrum: (MeOD, 400 MHz) 7.4 (t, 2H), 7.6 (t, 1H), 7.7 (m, 4H), 8.1 (d, 2H)*.

*Data for non-labelled compound

$^{14}$C-labelled 4-Benzoyl-(5-fluorophenyl)benzoate (3.3)

Intermediate 25

Intermediate 24 (211 mg, 0.92 mmol) and pentafluorophenol (185 mg, 1.0 mmol) were taken up in ethyl acetate (5 ml). The solution was cooled to 10–15° C. while under nitrogen. 4-Dimethylaminopyridine (4 mg) was added followed by the dropwise addition of 1,3-dicyclohexylcarbodiimide (206 mg, 1.0 mmol) in ethyl acetate (5 ml). The resulting solution was stirred at 10–15° C. for 2 hours. On return a thick white precipitate had formed which was presumed to be 1,3-dicyclohexylurea. The 1,3-dicyclohexylurea was removed by filtration and the precipitate washed with ethyl acetate (50 ml). The organics were then washed sequentially with 2N sodium carbonate (20 ml) and brine (10 ml). The organic layer was dried (sodium sulphate) and concentrated under reduced pressure to give an off white solid. The crude product was purified by silica column chromatography eluting with isohexane-ethyl acetate (100:10) to give the title compound (3.3) as a white solid (288 mg, 79%). Co-elutes with authentic 4-benzoyl-(5-fluorophenyl)benzoate.

TLC(Merck 5714): isohexane-ethyl acetate (4:1), $R_f$=0.5*. $^1$H NMR: (CDCl$_3$, 400MHz) 7.5 (t, 2H), 7.6 (t, 1H), 7.8 (d, 2H), 7.9 (d, 2H), 8.3 (d, 2H)*.

Data for non-labelled compound

4'-Chloro-biphenyl-4-carboxylic Acid

Intermediate 26

To a solution of 20 g (0.1 mol.) of 4-bromo benzoic acid in toluene (300 mL) was added successively 3.5 g (0.03 equiv.) of tetrakis (triphenylphosphine) palladium (0), 50 ml (1 eq.) of a 2M solution of Na$_2$CO$_3$ and 12.9 g (3 eq.) of lithium chloride. After 15 minutes of stirring was added a solution of 10.8 g (1.2 eq.) of 4-chlorophenyl boronic acid in EtOH (120 mL). Then, the mixture was refluxed for 24 hours. After cooling, the solvents were evaporated to dryness. The residue was poured in water (300 mL) and the aqueous layer was acidified to pH=1 with a 1N HCl solution. After filtration, the solid was washed with water and dried to give a crude solid which was recrystallized in 2-methoxy ethanol to give after drying 15 g of 4-(4-chlorophenyl) benzoic acid as a white powder in a 64.4% yield.

MP: 290–291° C.

1-[4-(1-Hydroxy-naphtalen-2-yl)-3,6-dihydro-2H-pyridin-1-yl]-ethanone

Intermediate 27

To a solution of 1-Naphtol (30.0 g, 0.21 mol) and 1-Acetyl-4-piperidone (29.4 g, 1.0 eq.) was added dropwise BF$_3$-Et$_2$O (100 mL, 4.0 eq). The mixture was stirred at 100° C. for 48 hours. After cooling to rt, the mixture was treated with a 1N HCl solution (400 mL). The resulting solution was extracted with DCM. The organic layer was dried over Na$_2$SO$_4$ and evaporated to dryness to give a solid which was recrytallized in MeCN to give the title compound (30.0 g, 0.11 mol) as a white powder in a 54% yield.

GC/MS: M+C$_{17}$H$_{17}$NO$_2$ 267.

1-[4-(1-Hydroxy-naphtalen-2-yl)-piperidin-1-yl]-ethanone

Intermediate 28

A solution of intermediate 27 (30.0 g, 0.112 mol) in a mixture of cyclohexene (200 mL), MeOH (100 mL), THF (150 mL) was treated with Pd(OH)$_2$, 20% (8 g). The resulting solution was allowed to stir at reflux for 4 days. After cooling, the reaction mixture was filtered through a bed of celite. The filtrate was evaporated to dryness to give the title compound as a yellow solid (24.9 g, 0.09 mol) in a 82% yield.

GC/MS: M+C$_{17}$H$_{19}$NO$_2$ 269.

1-[4-(1-Methoxy-naphtalen-2-yl)-piperidin-1-yl]-ethanone

Intermediate 29

To a solution of intermediate 28 (22.0 g, 0.08 mol) in dry DMF (200 mL) was added K$_2$CO$_3$ (23.0 g, 2 eq.) and methyl iodide (21 mL, 4 eq.). The reaction was stirred at 80° C. for 16 hours. After cooling, the reaction was filtered off and evaporated under reduced pressure. The oil was diluted with DCM and washed with water. The organic layer was dried over Na$_2$SO$_4$ and evaporated to dryness to give the title compound as a white solid in a quantitative yield.

GC/MS: M+C$_{18}$H$_{21}$NO$_2$ 283.

4-(1-Methoxy-naphtalen-2-yl)-piperidine

Intermediate 30

To a solution of 23.0 g (82 mmol) of the intermediate 29 in EtOH (300 mL) was added dropwise a 1/1 solution of 35% NaOH and H$_2$O (100 mL). The resulting mixture was stirred at 100° C. during 18 hours. After cooling to rt and evaporation under reduced pressure, the residue was taken up in DCM and washed with water. The organic phase was dried over Na$_2$SO$_4$ and evaporated off to give 10.6 g (44 mmol) of the title compound as an oil.

GC/MS: M+C$_{16}$H$_{19}$NO 241.

2-{4-[4-(1-Methoxy-naphtalen-2-yl)-piperidin-1-yl]-butyl}-isoindole-1,3-dione

Intermediate 31

A solution of intermediate 30 (10.6 g, 0.044 mol) in acetone (200 mL) was treated with K$_2$CO$_3$ (12.13 g, 2.0 eq.) and N-(4-Bromobutyl)-phtalimide (12.4 g, 1.0 eq.). The resulting mixture was stirred under reflux for 16 hours. After cooling to rt the reaction mixture was filtered off. The cake was washed with acetone. The filtrate was evaporated off. The residue was flash chromatographed using DCM/MeOH (95/5) as eluent to give the title compound (17.1 g, 0.039 mol) as a yellow oil in a 88% yield.

LC/MS (APCI): [M+H+]443 C$_{28}$H$_{30}$N$_2$O$_3$.

4-[4-(1-Methoxy-naphtalen-2-yl)-piperidin-1-yl]-butylamine

Intermediate 32

A solution of intermediate 31 (17.1 g, 0.039 mol) in MeOH (300 mL) was treated with hydrazine hydrate (10 mL, 4.0 eq.). The resulting mixture was stirred at reflux for 16 hours. After evaporation under reduced pressure the residue was dissolved in a minimum quantity of water and treated with a concentrated HCl solution until PH=3–4. Then the cake was filtered and washed with water. The aqueous filtrate was saturated with a concentrated NaOH solution. Extraction with DCM/MeOH (99/1), drying over Na$_2$SO$_4$ and filtration gave the title compound (11.7 g, 0.037mol) as a yellow oil in a 97% yield.

LC/MS (APCI): [M+H+]313 C$_{20}$H$_{28}$N$_2$O.

Example 1

4-(4-Chloro-benzoylamino)-N-{4-[4-(2-ethoxy-4-ethyl-phenyl)-piperidin-1-yl]-butyl}-benzamide A solution of intermediate 10 (6.8 g, 0.022 mol) in DMF was treated with intermediate 2 (1.1 eq.), EDCI (1.1 eq.), HOBt (1.1 eq.) and TEA (1.1 eq.). The resulting mixture was stirred for 16 hours at rt. The solvent was evaporated off. The residue was taken up in DCM and washed with a 1N NaOH solution and brine. The organic layer was dried over $Na_2SO_4$ and evaporated off. The residue was flash chromatographed using MeOH/DCM (10/90). Recrystallization from DMF gave the title Example 2 s white crystals in a 52% yield.

MP: 250° C. Analysis for $C_{33}H_{40}ClN_3O_3$ (0.3 DMF); Calculated: C, 69.71; H, 7.26; N, 7.91. Found: C, 69.56; H, 7.37; N, 7.7.

Example 2

4-(4-Benzoyl)-N-{4-[4-(4-isopropyl-2-methoxy-phenyl)-piperidin-1-yl]-butyl}-benzamide Hydrochloride A solution of intermediate 18 (0.2 g, 0.66 mmol) in DMF (5 mL) was treated with 4-Benzoylbenzoic acid (0.15 g, 1.0 eq.), EDCI (1.5 eq.), HOBt (1.5 eq.) and TEA (1.5 eq.). The resulting mixture was stirred for 16 hours at rt. The solvent was evaporated off. The residue was taken up in DCM and washed with a 1N NaOH solution and brine. The organic layer was dried over $Na_2SO_4$ and evaporated off. The residue was dissolved in a minimum amount of hot DMF and treated with a 1N HCl solution to give the title compound as a white solid in a 34% yield.

MP: 138° C. Analysis for $C_{33}H_{40}N_2O_3$ (2 HCl); Calculated: C, 67.68; H, 7.23; N, 4.78. Found: C, 67.59; H, 7.68; N, 4.94.

$^{14}$C-labelled Example 2

4-(4-Benzoyl)-N-{4-[4-(4-isopropyl-2-methoxy-phenyl)-piperidin-1-yl]-butyl}-benzamide 4-Benzoyl-(5-fluorophenyl)-benzoate (3.3) (288 mg, 0.73 mmol) and 4-[4-(4-isopropyl-2-methoxy-phenyl)-piperidin-1-yl]-butylamine (3.4) (244 mg, 0.8 mmol) were taken up in chloroform (6 ml) and warmed at 55° C. for 2 hours under nitrogen. The solution was then concentrated under reduced pressure for 2 hours to remove the bulk of the 5-fluorophenol produced in the reaction. The crude product was purified by silica column chromatography eluting initially with dichloromethane-ethanol (90:10) then with dichloromethane-ethanol-ammonia (150:5:0.5). After combining the column fractions they were found to contain 5-fluorophenol as it's ammonium salt. The product was taken up by ethyl acetate (150 ml) and washed with 0.75 M sodium hydroxide (3×15 ml). The organic layer was dried (sodium sulphate) and concentrated under reduced pressure to give the title compound as an off white solid (200 mg, 53%).

Mass Spectrum: (electrospray) MH$^+$515; TLC (Merck 5714): dichloromethane-ethanol-ammonia (150:5:0.5) $R_f$=0.2. $^1$H NMR spectrum: (CDCl$_3$, 400MHz) 1.2 (d, 6H), 1.7 (m, 8H), 2.1 (br t 2H), 2.5 (t, 2H), 2.9 (m, 2H), 3.1 (brt, 2H), 3.5 (br q, 2H), 3.8 (s, 3H), 6.7 (s, 1H), 6.75 (d, 1H), 6.9 (d, 1H), 7.5 (br t, 3H), 7.6 (t, 1H), 7.7 (d, 2H), 7.85 (d, 2H), 7.95 (d, 2H).

Example 3

3-Ethoxy-11-hydroxy-androst-3,5-diene-17α,17β-(1,3,6,8-tetraoxaspiro[4.4]nonan-4-yl)-6-methyldimethylamine A solution of Intermediate 22 (3.39 g, 0.007 mol) in dry THF (50 mL) was added the LiAlH$_4$ (1M in Et$_2$O solution, 3.48 mL, 0.5 eq.) and the reaction was stirred for 16 hours at rt. The reaction was treated slowly with H$_2$O and the product was extracted with AcOEt. The organic layer was washed with H$_2$O, brine, dried over Na$_2$SO$_4$ and evaporated off. Purification by chromatography on silica gel (EtOAc and MeOH) give the title compound as a solid (0.67 g, 0.0014 mol) in a 19.5% yield.

MP: 93–95° C.; Analysis for $C_{28}H_{43}NO_6$ (0.8H$_2$O); Calculated: C, 66.72; H, 8.92; N, 2.78. Found: C, 66.5; H, 8.76; N, 2.57.

Example 4

4'-Chloro-biphenyl-4-carboxylic Acid{4-[4-(1-methoxy-naphtalen-2-yl)-piperidin-1-yl]-butyl}-amide To a solution of intermediate 31 (1.1 g, 4 mmol) in dry DCM (20 mL) was added the intermediate 26 (0.96 g, 0.95 eq.), EDCI (1.2 g, 1.5 eq.), HOBt (0.86 g, 1.5 eq.) and TEA (0.7 mL, 1.5 eq.). The resulting mixture was stirred for 16 hours at rt. The solution was washed with a 1N NaOH solution and brine. The organic layer was dried over Na$_2$SO$_4$ and evaporated off. Recrystallization from CH$_3$CN gave the title compound as white crystals in a 72% yield.

MP: 197° C. LC/MS: [M+H+]527 $C_{33}H_{35}ClN_2O_2$.

Biological Experimental Methods

Materials

Fetal bovine serum and CCM-3 medium were obtained from Hyclone and all other culture medium and additives were from Life Technologies, Inc. Super competent DH5-α cells, Platinium Pfx DNA polymerase, Gateway cloning system, pDonR201, pDest10, competent DH10Bac *E. Coli* cells, restriction enzymes and T4 ligase were from Life Technologies, Inc. Baculovirus transfer vector pTen12 was from Quantum Biotechnologies Inc. T7-tag and HSV-tag monoclonal antibodies and STP-3 in vitro translation kit were from Invitrogen. Human LDL and human Dil-LDL were from Biomedical Technologies Inc. HepG2 cells, Sf-9 cells were from the American Type Culture Collection. The vectors pTK-HSV-SCAP-T7 and pTK-HSV-BP-2 were obtained from American Type Culture Collection *E. Coli* respectively clone 63365 and 99530. All other reagents were from Sigma.

Expression of SCAP

Hamster SCAP cDNA was cut from pTK-HSV-SCAP-T7 using BglII and Xbal and re-cloned in pTen 12 transfer vector. Recombinant baculovirus clones were produced by Quantum Biotechnologies Inc. and screened by western blots using T7-tag antibodies on Sf-9 infected cells. Sf-9 cells were grown in CCM-3 medium at 28° C. and seeded at 8×10$^6$ cells per 75 cm$^2$ flask. Four hours later they were infected with 200×10$^6$ pfu of baculovirus and incubated 3 days before harvest. Truncated SCAP corresponding to amino acid 2 to 473 was produced by PCR amplification with Platinium Pfx polymerase using pTK-HSV-SCAP-T7 as template and primers containing attB1 sequence followed by SEQ ID NO: 1 CCCTGACTGAAAGGCTGCGT-GAGAA and the complement strand of attB2 sequence followed by SEQ ID NO: 2 CATAGCGTGCTGGCCTTC-CCACA. After recombination into pDonR201 vector using the Gateway cloning system, the inserts were recloned into pDest10 vector using LR recombinase. The corresponding bacmids and recombinant baculovirus were produced according the manufacturer instructions.

In vitro translation of SCAP was performed using pTK-HSV-SCAP-T7 plasmid and STP-3 kit with L-[$^{35}$S]-methionine according to the manufacturer instruction.

Assay for Determination of SCAP Binding

A competition binding assay using recombinant SCAP protein was developed in Sf-9 insect cells. A recombinant baculovirus coding for full length hamster SCAP was used to express the protein. Alternatively, a truncated form of SCAP corresponding to amino acid 2 to 473 was expressed using the baculovirus system.

Infected Sf-9 cells were harvested, washed in Dulbecco phosphate buffered saline and $2 \times 10^5$ cells were incubated with test compounds and the control ($^{14}$C radio-labeled Example 2) for 30 min at 28° C. in 24 well plates. Ultra violet light irradiation was performed for 10 min at 4° C. using a 6 W 365 nm VL-6.LP lamp (Vilbert-Lourmat). Cells were pelleted by centrifugation and lysed in Laemli sample buffer. In some experiments, membrane fraction was obtained by sonicating cells at 20 kHz for 2 seconds followed by centrifugation at 8000 g for 10 minutes. 10 µg of protein were loaded on a 8% acrylamide SDS-PAGE and dried. The radioactivity was detected using a PhosporImager screen (Molecular Dynamics).

Assay for Determination of LDL-receptor Transcription

The human LDL-receptor promoter named p-588 corresponding to nucleotide −588 to +91 relative to the major transcription site was cloned by PCR from human genomic DNA (Clonetech) using SEQ ID NO: 3 GAAGATCTA-CAAAACAAAAAATATTTTTTGGC and SEQ ID NO: 4 GGCCCCATGGTCGCAGCCTCTGCCCAG-GCAGTGTCC primers. and inserted into pGL3-basic vector (Promega) at Hind-III and Nco-I sites. The sequencing was identical to published promoter (Genbank L29401). Shorter promoters were obtained by PCR sub-cloning using Kpn-I and Nar-I sites. The primer SEQ ID NO: 5 CAATTGTTC-CAGGAACCAGG corresponding to luciferase coding sequence was used as reverse primer for all constructs. The following primers were used to produce respectively p-149, p-118, p-70, p-53 and p-31 promoters: SEQ ID NO: 6 GGGGTACCAATCAGAGCTTCACGGGTTAAAA, SEQ ID NO: 7 GGGGTACCACATCGGCCGTTCGAAACTC, SEQ ID NO: 8 GGGGTACCTGAAAATCACCCCACTGCAAACT, SEQ ID NO: 9 GGGGTACCAAACTCCTCCCCCTGCTA-GAAA and SEQ ID NO: 10 GGGGTACCTCACAT-TGAAATGCTGTAAATGA. A vector containing the 38 bp of the minimal promoter of adenovirus Major Late Promoter (Ham. J. et al., EMBO, 10: 2931–2940 (1991)) was produced using Bgl-II and Hind-III site in pGL3-basic. Four repeats of the SRE sequence present on the human LDL-receptor promoter were introduced in p-MLP vector using Bgl-II site, SEQ ID NO: 11 GATCTAAAATCACCCCACT-GCAAAATCACCCCACTGCA and complementary oligo. HepG2 cells seeded the previous day at $3 \ 10^5$ cells per well of 24 well plate were transfected with 1 µg of LDL-promoter containing vector together with p-RL-TK control vector (Promega) using Fugene 6 (Boehringer). HepG2 cells were incubated for 28 hours in the presence of SCAP antagonist and/or 25OH-cholesterol. Firefly luciferase and Renila activity were measured using Dual Luciferase Assay Kit (Promega) and Lumistar (BMG). The ratio of Firefly luciferase to Renila were used to calculate mean and S.D. of tetraplicates.

Western Blot Analysis of the Proteolytic Maturation of SREBP-2

The involvement of the SREBP pathway was confirmed by Western Blot immunodetection of precursor and mature forms of human SREBP-2.

HepG2 cells were seeded in 150 cm$^2$ flasks at $8 \times 10^6$ cells and transfected with 10 µg of pTK-HSV-BP2 using Fugene 6 and incubated for 20 h before addition of 1 µM of example 1 or vehicle. After 18 h of incubation, membrane fraction and nuclear extracts were obtained using the method described by Hua, X. et al., J. Biol. Chem. 270: 29422–27 (1995).

Proteins (20 µg/load) were separated on 8% SDS-PAGE and blotted onto BA 83 nitrocellulose membrane (Schleisher & Schuell). The HSV tag present in the amino terminus of SREBP-2 was detected using 0.2 µg/ml of anti-HSV antibodies after saturation with 10% non-fat milk. After incubation for 2 h with anti-Mouse peroxidase conjugate (Pierce), the western blot was revealed with Supersignal femto (Pierce) and CCD camera IS440CF (Kodak).

Assay to Determine Uptake of Dil-LDL

To determine if activation of LDL-receptor promoter also translated into an increase in functional LDL receptors, an LDL uptake assay was set up. HepG2 cells seeded at $8 \ 10^4$ cells per 8 well Biocoat slides (Beckton Dickinson) were treated with SCAP antagonist or 25OH-cholesterol for 20h and then incubated with 6 µg/ml of fluorescent Dil-LDL for 4 hours. The amount of fluorescent dye that accumulated in the lysosomes was quantified by fluorescence microscopy using Axioplan-2 Zeiss microscope equipped with DXC950P video camera (Sony) and red fluorescence filters.

Treatment of Hamster with SCAP Antagonist

The in vivo activity of SCAP antagonist was determined in the golden Syrian hamster previously fed with a cholesterol rich diet. Male Syrian golden hamsters (Janvier, France) were kept on a 12 h light-dark cycle. Animals (7 weeks age, 150 g) were fed for 2 weeks with a high cholesterol diet containing 0.2% cholesterol plus 10% coconut oil. Animals (n=5 per group) were then treated orally with vehicle, (0.5% methylcellulose, 5% Tween 80) or Example 1 at 1, 5 or 20 mg/kg in the vehicle, once a day for 3 days.

Quantification of LDL-receptor mRNA by Real-time PCR in Hamster Livers 4 hours after the last administration, animals were sacrificed and livers were immediately dropped into liquid nitrogen. Total RNA was extracted using RNAqous kit (Ambion) according to manufacturer instruction. The Taqman reverse transcription kit (Perkin Elmer) was used to produce cDNA from 1 µg of RNA (random hexamers). Real time PCR was performed on Abi Prism 7700 (PE Applied Biosystems) using Master Mix SYBRgreen kit (PE Applied Biosystems) in 25 µl total volume with 300 nM of primers and according to manufacturer instruction. The expression of the hamster LDL-receptor was determined using the following primers: SEQ ID NO: 12 AAGACACATGCGACAGGAATGAG and SEQ ID NO: 13 GACCCACTTGCTGGCGATAC. Taqman Ribosomal RNA (18S) control reagent (Perkin Elmer) was used as the internal reference gene. Each sample was quantified in duplicates and the cycle threshold (Ct) were calculated. For each animal the difference between Ct values for the LDL-receptor and Ribosomal RNA were calculated. The quantity of LDL-receptor mRNA relative to Ribosomal RNA reference was calculated as $2^{-\Delta\Delta Ct}$ and expressed in arbitrary units.

Determination of Lipoprotein and Lipid in Hamster Sera 4h after the last treatment, animals were anesthetized, blood was collected and serum was prepared by centrifugation. Total cholesterol was determined using a enzymatic assay kit (Biomerieux, France). Lipoproteins were separated by ultracentrifugation using a single KBr concentration (density 1.063). Cholesterol and triglycerides associated with the upper phase (corresponding to VLDL +LDL lipoproteins) and cholesterol associated with the lower phase (corresponding to the HDL fraction) were determined using the enzymatic assays kits. Apolipoprotein B100 associated with VLDL and LDL lipoprotein fraction were analysed by SDS-PAGE and Coomassie blue staining. Lipoproteins were also separated by high-performance gel filtration chromatography with on-line colorimetric determination of cholesterol. Lipoprotein separation was performed on a single superose 6HR column (Pharmacia) with an elution buffer consisting of 10 mM tris, 1 mM EDTA and 150 mM NaCl adjusted at pH 7.4. Cholesterol was measured on line using the RTU enzymatic assay (Biomerieux). The column was calibrated using human lipoproteins and the various peaks in cholesterol profiles are designated VLDL, LDL and HDL for simplicity.

Biological Results

Evidence of Binding Competition on SCAP

Sf-9 insect cells were infected with recombinant baculovirus encoding for full length hamster SCAP containing a T7 tag (FIG. 1A). Total protein (10 µg) from control cells (lanes b, d) or infected cells (lanes a, c) were analyzed by SDS-PAGE and either stained using Coomassie blue (lanes a, b) or blotted on nitrocellulose membrane following immuno-detection with T7 tag monoclonal antibody (lanes c, d). Infected cells were incubated for 30 min at 28° C. in the presence of 5 µM of $^{14}$C-Example 2 before 365 nm ultra-violet light irradiation for 10 min (lanes f to l). Control condition (lanes h, i) was compared to 5 and 10 fold isotopic dilution with $^{12}$C-Example 2 (lanes f, g) or in the presence of 100, 50, 20 µM of Example 3 (lanes j to l). In vitro translation of SCAP using $^{35}$S-methionine was used as a size control (lane e). The gel was dried and radioactivity detected using Phosphor Imager Screen.

As shown in FIG. 1A, after 365 nm UV light irradiation, radio-labelled photo-activable Example 2 specifically labeled SCAP. In the presence of Example 3, a sterol-like compound, the labelling was displaced in a dose dependant manner. This evidence clearly indicates that the two chemically unrelated compounds bind on SCAP and are competing on the same site. Thus, binding competition with radio-labelled Example 2 may be used as the basis for the screening of SCAP antagonists.

Sf-9 cells were infected with a recombinant baculovirus encoding for a truncated form of SCAP corresponding to amino acid 2 to 473 (FIG. 1B). After photo-affinity labelling with 5 µM of $^{14}$C-Example 2, membranes were analyzed using SDS-PAGE as above. Control condition (lane m) was compared to labelling in the presence of 200 µM or 100 µM of Example 3 (lane n, o). As shown in FIG. 1B, a truncated form containing the putative sterol sensing domain can be labelled by Example 2 in a manner that is competitive with Example 3.

SCAP Antagonist Promote LDL-receptor Promoter Activation

A vector containing the human LDL-receptor promoter coupled to Firefly luciferase reporter was made. A mixture of the LDL-receptor vector and control pRL-TK vector was used to transfect HepG2 cells. Cells were incubated with 25OH-cholesterol (0.2 or 1 µM) alone or in the presence (black bars) or absence (gray bars) of Example 1 (1 µM) for 28 hours before measurement of luciferase and renila activity. The ratio of luciferase activity versus renila activity was calculated and the mean and SD of triplicates were expressed as percent of control.

As shown in FIG. 2, mimicking cholesterol loading of the cell by incubation with 25-OH-cholesterol, represses LDL-receptor promoter activity. By contrast, Example 1 acts as a transcriptional activators. Thus the LDL-receptor promoter activity may be modulated over a 17-fold range. Co-treatment of cells with Example 1 and 25OH-cholesterol clearly indicates that Example 1 can at least partially antagonise the effects of 25OH-cholesterol on SCAP and is able to activate the LDL-receptor promoter even in the presence of the repressor sterols. Thus SCAP antagonist does not abolish the physiological regulation of LDL-receptor but rather displace the equilibrium to a more activated state.

The Effect of SCAP Antagonist on LDL-receptor Promoter is Mediated by SRE

Shortening the LDL-receptor promoter in the same reporter vector modifies the relative luciferase activity (FIG. 3A). Addition of Example 1 (1 µM) to HepG2 transfected cells promote expression only for vectors possessing the SRE sequence (FIG. 3B, left). When repression by 25OH-cholesterol is measured, two sequences are involved: SRE and FP-1 (FIG. 3B right). The vector containing the minimal promoter containing 38 bp of adenovirus Major Late promoter (p-MLP) fails to respond to Example 1 (1 µM) whereas the introduction of 4 copies of SRE is sufficient to confer the responsiveness to this SCAP antagonist (FIG. 3C).

SCAP Antagonist Increases the Proteolytic Maturation of SREBP-2

HepG2 cells were transfected (FIG. 4, lane b–e) or not transfected (FIG. 4, lane a) with pTK-HSV-BP2 vector encoding human SREBP-2 preceded by HSV tag. Cells were treated for 18 hours with Example 1 (1 µM) (lane c, d) or vehicle (lane a, b, e) and nuclear extract (lane d, e) and membrane (lane a–c) were isolated and analysed by western blotting using anti-HSV antibodies. As shown in FIG. 4, Example 1 reduces the amount of SREBP-2 precursor form present in the membrane (lane c versus b). Simultaneously, Example 1 strongly increases the amount of mature SREBP-2 in the nucleus (lane d versus e). Although the gray scale was adjusted in the nuclear extracts (30 fold) to allow visulization of the mature form, this indicates that Example 1 increases the proteolytic maturation of SREBP-2.

LDL Uptake is Stimulated by SCAP Antagonist

HepG2 cells were treated for 24 hours in the presence of 0.5 µM Example 1 or 10 µM 25OH-cholesterol. Dil-LDL (6 µg/ml) were added 4 hours before the end of the incubation. Cells were washed and observed by fluorescence microscopy using rhodamine filters and video camera with fixed settings.

As shown in FIG. 5, Example 1 markedly increased the LDL uptake by HepG2 cells, whereas 25-OH-cholesterol reduced it. This clearly demonstrates that Example 1, by increasing LDL receptor expression, could stimulate the function of LDL receptor i.e. the uptake of LDL.

SCAP Antagonist Increases LDL-receptor mRNA in the Liver of Fat-Fed Hamsters

Cholesterol-fed hamsters were treated with Example 1 (5 mg/kg) or vehicle for 3 days. LDL-receptor mRNA in the liver was quantified by real-time PCR using Ribosomal 18S RNA as internal reference. As shown in FIG. 6, animals treated with Example 1 (black bars) have increased mRNA for LDL-receptor when compared to control animals (grey bars). This demonstrates that SCAP antagonist increases LDL-receptor expression in vivo despite a high intake of cholesterol SCAP Antagonist Lowers LDL-Cholesterol, Triglycerides and Apo-B100 Levels in Fat-Fed Hamsters Cholesterol-fed animals were treated for 3 days with Example 1 at 1 and 20 mg/kg. As shown in Table 1, Example 1 reduces both LDL-cholesterol and triglycerides by respectively 50% and 63% at 1 mg/kg and by 83% and 76% at 20 mg/kg. Apolipoprotein B100 is also reduced to the same extent while HDL-cholesterol is unaffected. In another experiment, lipoproteins were separated by gel filtration and cholesterol content was quantified on-line. As shown in FIG. 7 Example 1 at 5 mg/ml strongly reduces atherogenic particles: 79% reduction of VLDL cholesterol and 60% reduction of LDL-cholesterol. On the opposite, the cholesterol contained in protective HDL particles were slightly increased (25%). This indicates that Example 1, antagonising the effect of cholesterol, was able to strongly up-regulate LDL-receptor expression even in the presence of excess cholesterol provided by the diet and in doing so, induces a very favourable lipoprotein profile.

TABLE 1

| | CHOLESTEROL (g/l) | | | Triglycerides (g/l) | apoB100 |
|---|---|---|---|---|---|
| | TOTAL | LCLchol | HDL chol | TOTAL | (S.U.) |
| CONTROL | 3.9 ± 0.5 | 1.9 ± 0.5 | 1.23 ± 0.2 | 3.5 ± 1 | 5 ± 0.7 |
| Example 1 1 mg/kg % of control | 3.1 ± 0.3 79% (p < 0.02) | 0.95 ± 0.2 50% (p < 0.01) | 1.5 ± 0.1 123% (p < 0.02) | 1.3 ± 0.2 37% (p < 0.001) | 3.1 ± 0.4 62% (p < 0.005) |
| Example 1 20 mg/kg % of control | 2.1 ± 0.3 55% (p < 0.001) | 0.3 ± 0.1 17% (p < 0.001) | 1.4 = 0.2 113% NS | 0.8 ± 0.02 24% (p < 0.001) | 1.2 ± 0.2 25% (p < 0.005) |

Tablet Compositions

The following compositions A and B can be prepared by wet granulation of ingredients (a) to (c) and (a) to (d) with a solution of povidone, followed by addition of the magnesium stearate and compression.

| | Composition A | mg/tablet | mg/tablet |
|---|---|---|---|
| (a) | Active ingredient | 250 | 250 |
| (b) | Lactose B.P. | 210 | 26 |
| (c) | Sodium Starch Glycollate | 20 | 12 |
| (d) | Povidone B.P. | 15 | 9 |
| (e) | Magnesium Stearate | 5 | 3 |
| | | 500 | 300 |

| | Composition B | mg/tablet | mg/tablet |
|---|---|---|---|
| (a) | Active ingredient | 250 | 250 |
| (b) | Lactose 150 | 150 | — |
| (c) | Avicel PH 101 | 60 | 26 |
| (d) | Sodium Starch Glycollate | 20 | 12 |
| (e) | Povidone B.P. | 15 | 9 |
| (f) | Magnesium Stearate | 5 | 3 |
| | | 500 | 300 |

| Composition C | mg/tablet |
|---|---|
| Active ingredient | 100 |
| Lactose | 200 |
| Starch | 50 |
| Povidone | 5 |
| Magnesium Stearate | 4 |
| | 359 |

The following compositions D and E can be prepared by direct compression of the admixed ingredients. The lactose used in composition E is of the direct compression type.

| Composition D | mg/tablet |
|---|---|
| Active ingredient | 250 |
| Magnesium Stearate | 4 |
| Pregelatinised Starch NF15 | 146 |
| | 400 |

| Composition E | mg/tablet |
|---|---|
| Active ingredient | 250 |
| Magnesium Stearate | 5 |
| Lactose | 145 |
| Avicel | 100 |
| | 500 |

| | Composition F (Controlled release composition) | mg/tablet |
|---|---|---|
| (a) | Active ingredient | 500 |
| (b) | Hydroxypropylmethylcellulose (Methocel K4M Premium) | 112 |
| (c) | Lactose B.P. | 53 |
| (d) | Povidone B.P.C. | 28 |
| (e) | Magnesium Stearate | 7 |
| | | 700 |

The composition can be prepared by wet granulation of ingredients (a) to (c) with a solution of povidone, followed by addition of the magnesium stearate and compression.

Composition G (Enteric-coated Tablet)

Enteric-coated tablets of Composition C can be prepared by coating the tablets with 25 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Composition H (Enteric-coated Controlled Release Tablet)

Enteric-coated tablets of Composition F can be prepared by coating the tablets with 50 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

(ii) Capsule Compositions

Composition A

Capsules can be prepared by admixing the ingredients of Composition D above and filling two-part hard gelatin capsules with the resulting mixture. Composition B (infra) may be prepared in a similar manner.

|  |  | mg/capsule |
|---|---|---|
| Composition B | | |
| (a) | Active ingredient | 250 |
| (b) | Lactose B.P. | 143 |
| (c) | Sodium Starch Glycollate | 25 |
| (d) | Magnesium Stearate | 2 |
| | | 420 |
| Composition C | | |
| (a) | Active ingredient | 250 |
| (b) | Macrogol 4000 BP | 350 |
| | | 600 |

Capsules can be prepared by melting the Macrogol 4000 BP, dispersing the active ingredient in the melt and filling two-part hard gelatin capsules therewith.

| Composition D | mg/capsule |
|---|---|
| Active ingredient | 250 |
| Lecithin | 100 |
| Arachis Oil | 100 |
| | 450 |

Capsules can be prepared by dispersing the active ingredient in the lecithin and arachis oil and filling soft, elastic gelatin capsules with the dispersion.

| Composition E (Controlled release capsule) | | mg/capsule |
|---|---|---|
| (a) | Active ingredient | 250 |
| (b) | Microcrystalline Cellulose | 125 |
| (c) | Lactose BP | 125 |
| (d) | Ethyl Cellulose | 13 |
| | | 513 |

The controlled release capsule composition can be prepared by extruding mixed ingredients (a) to (c) using an extruder, then spheronising and drying the extrudate. The dried pellets are coated with a release controlling membrane (d) and filled into two-part, hard gelatin capsules.

| Composition F (Enteric capsule) | | mg/capsule |
|---|---|---|
| (a) | Active ingredient | 250 |
| (b) | Microcrystalline Cellulose | 125 |
| (c) | Lactose BP | 125 |
| (d) | Cellulose Acetate Phthalate | 50 |
| (e) | Diethyl Phthalate | 5 |
| | | 555 |

The enteric capsule composition can be prepared by extruding mixed ingredients (a) to (c) using an extruder, then spheronising and drying the extrudate. The dried pellets are coated with an enteric membrane (d) containing a plasticizer (e) and filled into two-part, hard gelatin capsules.

Composition G (Enteric-coated Controlled Release Capsule)

Enteric capsules of Composition E can be prepared by coating the controlled-release pellets with 50 mg/capsule of an enteric polymer such as cellulose acetate phthalate, polyvinylacetate phthalate, hydroxypropylmethylcellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

(iii) Intravenous Injection Composition

Active ingredient 0.200 g

Sterile, pyrogen-free phosphate buffer (pH 9.0) to 10 ml

The active ingredient is dissolved in most of the phosphate buffer at 35–40° C., then made up to volume and filtered through a sterile micropore filter into sterile 10 ml glass vials (Type 1) which are sealed with sterile closures and overseals.

| (iv) Intramuscular injection composition | |
|---|---|
| Active ingredient | 0.20 g |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

| (v) Syrup composition | |
|---|---|
| Active ingredient | 0.25 g |
| Sorbitol Solution | 1.50 g |
| Glycerol | 1.00 g |
| Sodium Benzoate | 0.005 g |
| Flavour | 0.0125 ml |
| Purified Water q.s. to | 5.0 ml |

The sodium benzoate is dissolved in a portion of the purified water and the sorbitol solution added. The active ingredient is added and dissolved. The resulting solution is mixed with the glycerol and then made up to the required volume with the purified water.

| (vi) Suppository composition | mg/suppository |
|---|---|
| Active ingredient | 250 |
| Hard Fat, BP (Witepsol H15 - Dynamit NoBel) | 1770 |
| | 2020 |

One-fifth of the Witepsol H15 is melted in a steam-jacketed pan at 45° C. maximum. The active ingredient is sifted through a 200 lm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 lm stainless steel screen and, with continuous stirring, allowed to cool to 40° C. At a temperature of 38–40° C., 2.02 g aliquots of the mixture are filled into suitable plastic moulds and the suppositories allowed to cool to room temperature.

| (vii) Pessary composition | mg/pessary |
|---|---|
| Active ingredient (63 lm) | 250 |
| Anhydrous Dextrose | 380 |
| Potato Starch | 363 |
| Magnesium Stearate | 7 |
| | 1000 |

The above ingredients are mixed directly and pessaries prepared by compression of the resulting mixture.

| (viii) Transdermal composition | |
|---|---|
| Active ingredient | 200 mg |
| Alcohol USP | 0.1 ml |
| Hydroxyethyl cellulose | |

The active ingredient and alcohol USP are gelled with hydroxyethyl cellulose and packed in a transdermal device with a surface area of 10 cm$^2$.

What is claimed is:

1. A method for the treatment of a mammal, having elevated circulating levels of low density lipoprotein (LDL)-cholesterol, comprising administration of an effective LDL-cholesterol lowering amount of a Sterol Responsive Element Binding Protein (SREBP)-Cleavage Activating Protein (SCAP) antagonist, or a physiologically acceptable salt or solvate thereof.

2. A method according to claim 1, where said mammal has a condition selected from the group consisting of hypercholesterolemia, hypertriglyceridemia, hyperlipidemia, atherosclerosis, pancreatitis, non-insulin dependent diabetes mellitus (NIDDM), coronary heart disease and obesity.

3. A method according to claim 1 where said SCAP antagonist is a synthetic organic molecule.

4. A method for reducing elevated circulating levels of low density lipoprotein (LDL) cholesterol in a mammal in need thereof, said method comprising administering to said mammal an effective LDL-cholesterol lowering amount of a compound that:
   (a) binds to Sterol Responsive Element Binding Protein—Cleaveage Activating Protein (SCAP); and
   (b) increases the transcription of LDL receptor, compared to the transcription that would occur in the absence of said compound.

5. A method according to claim 4 where said mammal has been diagnosed with a condition selected from the group consisting of hypercholesterolemia, hypertriglyceridemia, hyperlipidemia, non-insulin dependent diabetes mellitus, atherosclerosis, pancreatitis, coronary heart disease, and obesity.

6. A method according to claim 4 where said SCAP antagonist is a synthetic organic molecule.

7. A method of reducing elevated circulating levels of triglycerides in a mammal in need thereof, said method comprising administering to said mammal an effective triglyceride lowering amount of a compound that:
   (a) binds to Sterol Responsive Element Binding Protein—Cleaveage Activating Protein (SCAP); and
   (b) increases the transcription of LDL receptor, compared to the transcription that would occur in the absence of said compound.

8. A method according to claim 7 where said mammal has been diagnosed with a condition selected from the group consisting of hypercholesterolemia, hypertriglyceridemia, hyperlipidemia, non-insulin dependent diabetes mellitus, atherosclerosis, pancreatitis, coronary heart disease, and obesity.

9. A method according to claim 7 where said SCAP antagonist is a synthetic organic molecule.

10. A method for the treatment of a mammal, having elevated circulating levels of triglycerides, comprising administration of an effective triglyceride-lowering amount of a Sterol Responsive Element Binding Protein (SREBP)-Cleavage Activating Protein (SCAP) antagonist, or a physiologically acceptable salt or solvate thereof.

11. A method according to claim 10, where said mammal has a condition selected from the group consisting of hypercholesterolemia, hypertriglyceridemia, hyperlipidemia, atherosclerosis, pancreatitis, non-insulin dependent diabetes mellitus (NIDDM), coronary heart disease, and obesity.

12. A method according to claim 10 where said SCAP antagonist is a synthetic organic molecule.

13. A method for decreasing circulating levels of low density lipoprotein (LDL)-cholesterol in a mammal in need thereof, comprising:
   a) synthesizing a SCAP antagonist suitable for administration to a mammal;
   b) preparing a pharmaceutical composition containing said SCAP antagonist; and
   c) administering an effective LDL-cholesterol lowering amount of said pharmaceutical composition to said mammal in need of such treatment.

14. A method according to claim 13, where said mammal has been diagnosed with a condition selected from the group consisting of hypercholesterolemia, hypertriglyceridemia, hyperlipidemia, atherosclerosis, pancreatitis, non-insulin dependent diabetes mellitus (NIDDM), coronary heart disease and obesity.

15. A method according to claim 13 where said SCAP antagonist is a synthetic organic molecule.

16. A method of decreasing circulating levels of triglycerides in a mammal in need thereof, comprising:
   a) synthesizing a SCAP antagonist suitable for administration to a mammal;
   b) preparing a pharmaceutical composition containing said SCAP antagonist; and
   c) administering an effective triglyceride-lowering amount of said pharmaceutical composition to said mammal in need of such treatment.

17. A method according to claim 16 where said mammal has been diagnosed with a condition selected from the group consisting of hypercholesterolemia, hypertriglyceridemia, hyperlipidemia, non-insulin dependent diabetes mellitus, atherosclerosis, pancreatitis, coronary heart disease, and obesity.

18. A method according to claim 17 where said SCAP antagonist is a synthetic organic molecule.

19. A method according to claim 16 where said SCAP antagonist is a synthetic organic molecule.

* * * * *